United States Patent [19]

Ohno et al.

[11] Patent Number: 4,912,100
[45] Date of Patent: Mar. 27, 1990

[54] PLATINUM COMPLEX, PROCESS FOR PREPARING SAME AND ANTITUMOR AGENT

[75] Inventors: Masaji Ohno; Masato Mutoh; Hisao Kondo, all of Kamakura; Keiichi Matsunaga, Okazaki, all of Japan

[73] Assignee: Toray Industries, Inc., Tokyo, Japan

[21] Appl. No.: 108,074

[22] Filed: Oct. 13, 1987

[30] Foreign Application Priority Data

Oct. 15, 1986 [JP] Japan .................. 61-243178
Feb. 19, 1987 [JP] Japan .................. 62-36720
Mar. 6, 1987 [JP] Japan .................. 62-50165

[51] Int. Cl.$^4$ .................. A61K 33/24; C07F 15/00
[52] U.S. Cl. .................. 514/184; 514/186; 549/210; 549/3
[58] Field of Search .................. 549/210, 3; 514/184, 514/186

[56] References Cited

U.S. PATENT DOCUMENTS 4,661,516  4/1987  Brown et al. .................. 549/210

Primary Examiner—Nicky Chan
Attorney, Agent, or Firm—Austin R. Miller

[57] ABSTRACT

A platinum complex represented by the formula:

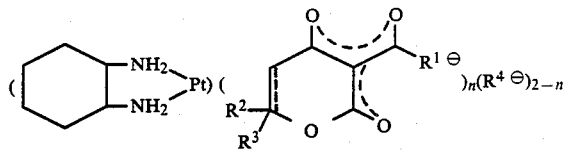

wherein $R^1$ is a (Cl–18) alkyl group, a (Cl–18)-alkenyl group or a group $-(-X-)-R^5$ in which X is —CH=CH— or a (Cl–5)alkylene group, and $R^5$ is a phenyl group, a hydroxyphenyl group, a (C7–12) alkoxyphenyl group, a halogenophenyl group, a nitrophenyl group, or (C8–13)alkoxycarbonylphenyl group, a cyclohexyl group having a (Cl—5)alkyl substituent,

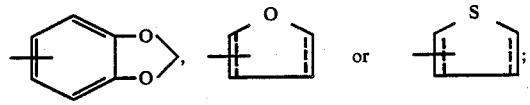

$R^2$ is a (Cl–18 alkyl group, $R^3$ is a hydrogen atom, or $R^2$ and $R^3$ are linked together to form a (C2–7)alkylene group, $R^4$ is OH or $NO_3$; the dotted line indicates that the bond may be either a single bond or a double bond; the chain line indicates a conjugated system; n is a number of from 1 to 2, and the 1,2-diaminocyclohexane moiety has a cis-, trans-l- or trans-d-configuration. This platinum complex is useful in the treatment of tumors.

9 Claims, No Drawings

PLATINUM COMPLEX, PROCESS FOR PREPARING SAME AND ANTITUMOR AGENT

BACKGROUND OF THE INVENTION (1) Field of the Invention

The present invention relates to novel platinum complexes, processes for the synthesis of the same, and pharmaceutical compositions for the treatment of malignant tumors which contains the same as the active ingredient.

(2) Description of the Related Art

The clinical application of cis-diamminedichloroplatinum(II) (hereinafter referred to as "CDDP") has recently brought marked progress in the chemotherapy of malignant tumors. Namely, CDDP shows a high anti-tumor activity towards cancers of sexual organs such as ovary and spermary. However, in clinical use, CDDP causes serious problems due to severe adverse effects including toxic effects on the kidney bone marrow. In this connection, kidney toxicity is generally considered to be a dose-limiting factor (DLF) in the clinical use of CDDP, and thus, a number of studies have been carried out to reduce the kidney toxicity or to seek other platinum complexes with a reduced toxicity. Platinum-(II) cis-diamine-1,1-cyclobutanedicarboxylate (hereinafter referred to as "CBDCA") and platinum(II) cis-diamine-O,O'-glycolate (see Japanese Unexamined Patent Publication No. 56-154,493, etc.) have been developed as a result of such studies and are regarded as the second generation of platinum antitumor agents.

These compounds do exhibit a reduced kidney toxicity, compared with CDDP, but their anti-tumor activity is also reduced compared with that of CDDP. Therefore, platinum complexes having a high anti-tumor activity and a low toxicity must be developed.

SUMMARY OF THE INVENTION

The primary object of the present invention is to provide novel platinum(II) complexes having a potent anti-tumor activity and a low toxicity, and to provide pharmaceutical compositions for the treatment of malignant tumors.

In one aspect of the present invention, there is provided a platinum complex represented by the following general formula (A):

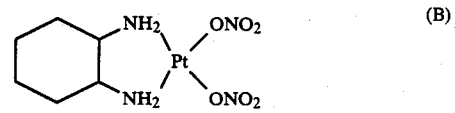

wherein $R^1$ is an alkyl or alkenyl group having 1 to 18 carbon atoms or a group $(-X)R^5$ in which X represents $-CH=CH-$ or an alkylene group having 1 to 5 carbon atoms, and $R^5$ is a phenyl group, a hydroxyphenyl group, an alkoxyphenyl group having 7 to 12 carbon atoms, a halogenophenyl group, a nitrophenyl group, an alkoxycarbonylphenyl group having 8 to 13 carbon atoms, a cyclohexyl group having an alkyl substitutent having 1 to 5 carbon atoms, or a group represented by the formula:

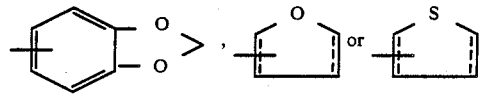

$R^2$ and $R^3$ are an alkyl group having 1 to 18 carbon atoms and a hydrogen atom, respectively, or linked together to form an alkylene group having 2 to 7 carbon atoms; $R^4$ represents OH or $NO_3$; the dotted line indicates that the bond may be either a single bond or a double bond; the chain line indicates a conjugated system; n is a number of from 1 to 2; and the 1,2-diaminocyclohexane moiety (hereinafter referred to as "dach") has a cis-, trans-l-or trans-d configuration.

In another aspect of the present invention, there is provided a pharmaceutical composition for the treatment of malignant tumors, comprising a therapeutically effective amount of a platinum complex represented by the general formula (A) and a pharmaceutically acceptable carrier therefor.

In still another aspect of the present invention, there is provided a process for preparing the platinum complex represented by the general formula (A), which comprises reacting a compound represented by the following formula (B):

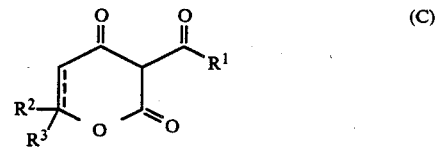

in the presence of an alkali metal hydroxide or an alkaline earth metal hydroxide with a compound represented by the following general formula (C):

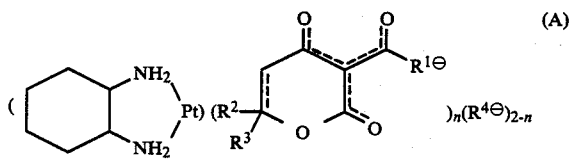

wherein $R^1$, $R^2$ and $R^3$ are as defined above.

In a further aspect of the present invention, there is provided a process for preparing the platinum complex represented by the general formula (A) wherein $R^4$ is OH, which comprises converting the compound represented by the formula (B) to a compound represented by the following formula (D) on an anion exchange resin:

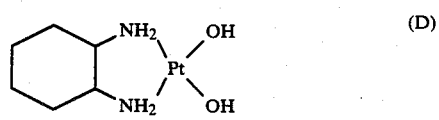

and then reacting the compound represented by formula (D) with a compound represented by the general formula (C).

In a still further aspect of the present invention, there is provided a process for preparing the platinum complex represented by the general formula (A), which comprises reacting a compound represented by the following formula (E):

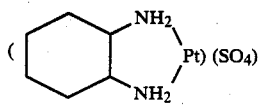 (E)

with a compound represented by the general formula (C) in the presence of an alkali metal hydroxide or an alkaline earth metal hydroxide.

DESCRIPTION OF THE PREFERRED EMBODIMENTS

In the platinum complexes of the general formula (A), a ligand of the following formula:

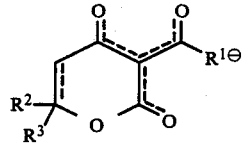

indicates a conjugated system represented by the following formulae:

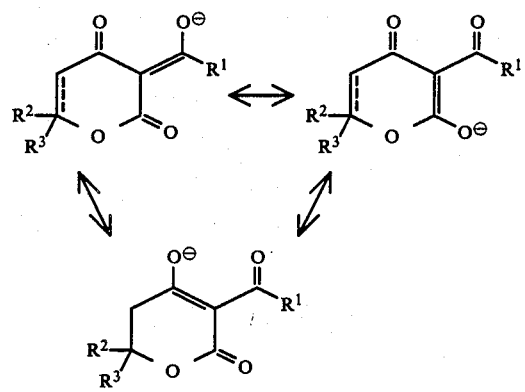

The platinum complexes of the general formula (A) may be prepared according to one of the following synthetic pathways.

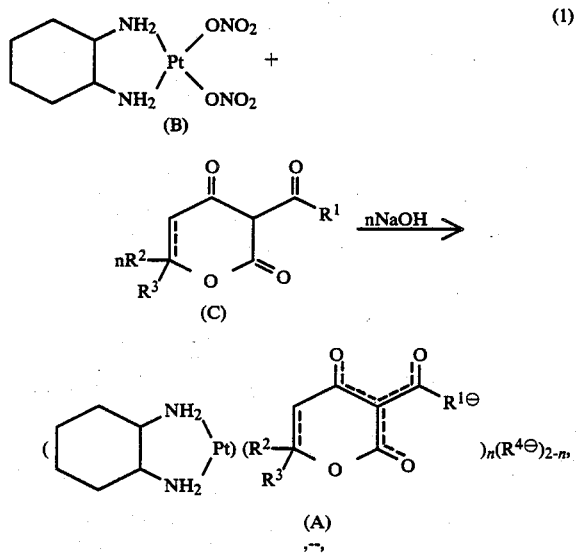

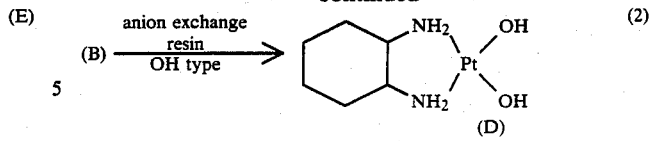

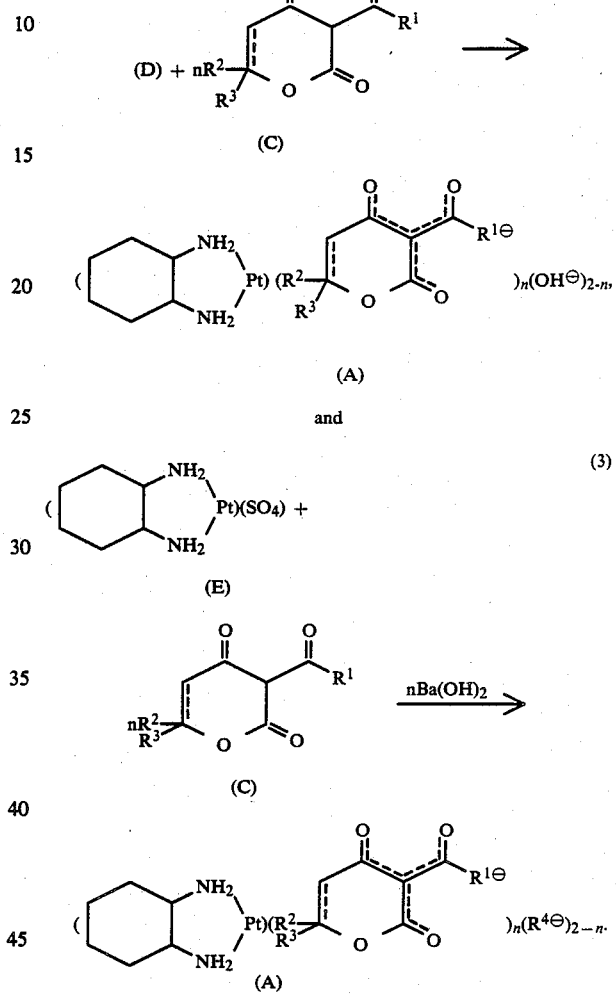

In the above-mentioned reaction formulae, $R^1$, $R^2$, $R^3$, $R^4$ and n are as defined above.

Namely, the compounds of the present invention can be obtained by (1) reacting dinitrato(1,2-diaminocyclohexane)platinum(II) hereinafter referred to as "compound (B)" with a compound (C) in the presence of an alkali metal metal hydroxide or an alkaline earth metal hydroxide; or (2) converting the compound (B) to dihydroxo(1,2-diaminocyclohexane)platinum(II) hereinafter referred to as "compound (D)" by passing an aqueous solution of the compound (B) through a column packed with an anion exchange resin (OH type) such as Amberlite IRA-400 (trademark) or Diaion SA-10A (trademark) and reacting the compound (D) with the compound (C), or (3) reacting sulfato(1,2-diaminocyclohexane)platinum(II) hereinafter referred to as "compound (E)" with the compound (C) in the presence of an alkali metal hydroxide or an alkaline earth metal hydroxide.

As the alkali metal hydroxide and alkaline earth metal hydroxide used in the processes (1) and (3), there can be mentioned sodium hydroxide, potassium hydroxide, barium hydroxide and calcium hydroxide. Of these, sodium hydroxide and potassium hydroxide are preferable in the process (1) and barium hydroxide is preferable in the process (3). Preferably, the amount of the alkali metal hydroxide or alkaline earth metal hydroxide is in the range of from approximately equivalent to the compound (c) to approximately twice the equivalent thereto in the process (1), and approximately equivalent to the compound (c) in the process (3).

The compounds (A) obtained by the reaction in an aqueous solution may contain water in the form of an aquo complex and such complexes are also included within the scope of the compounds of the present invention.

The compounds (B) and (E) used as the starting materials for the synthesis of the compounds of the present invention can be obtained by the reaction of a compound represented by the following formula (F):

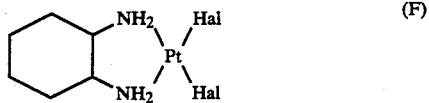

wherein Hal represents a halogen atom, with silver nitrate or silver sulfate, by utilizing a known technique, for example, the technique disclosed in Journal of Pharmaceutical Sciences, 65, 315 (1976).

The formula (F) indicates all the possible three isomers as the dach moiety, that is, Pt(cis-dach)Hal$_2$, Pt(trans-l-dach)Hal$_2$ and Pt(trans-d-dach)Hal$_2$ according to the configuration of the used 1,2-diaminocyclohexane ("dach" indicates 1,2-diamin19lclohexane).

The compounds (C) are the other starting compounds for the compounds of the present invention and can be synthesized according to the following processes disclosed in Japanese Unexamined Patent Publication No. 49-5,975 or Chemistry Letters, 1982, 1543–1546:

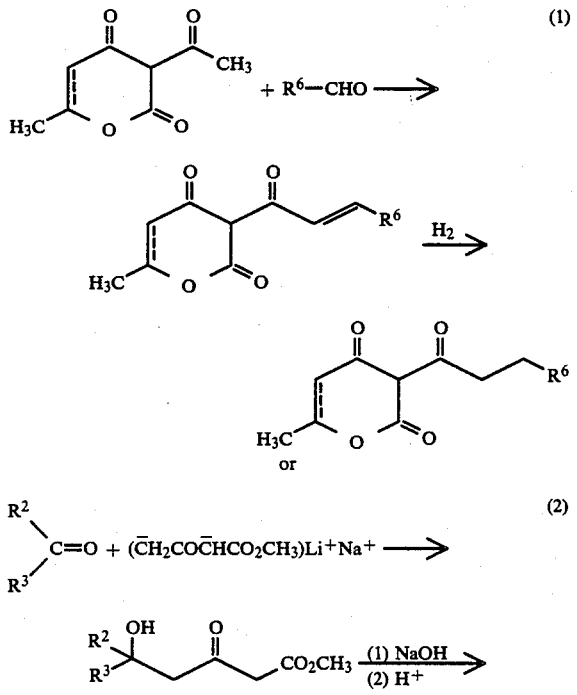

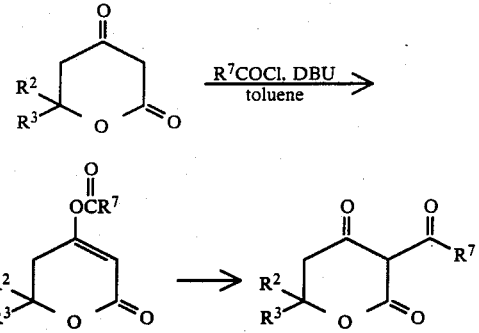

In the above reaction formulae, $R^2$ and $R^3$ are as defined above; $R^6$ is an alkyl or alkenyl group having 1 to 16 carbon atoms, a phenyl group, a hydroxyphenyl group, an alkoxyphenyl group having 7 to 12 carbon atoms, a halogenophenyl group, a nitrophenyl group, an alkoxycarbonylphenyl group having 8 to 13 carbon atoms, a cyclohexyl group having an alkyl substituent having 1 to 5 carbon atoms, or a group represented by the formula:

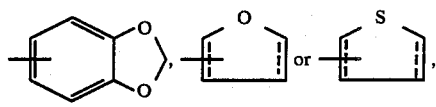

and $R^7$ is an alkyl group having 1 to 18 carbon atoms or an aryl group.

Preferred examples of the compound of the present invention are 3-acetyl-6-methyltetrahydropyran-2,4-dione-hydroxo(trans-l-1,2-diaminocyclohexane)-platinum(II) monohydrate, 3-acetyl-6-methyl-2H-pyran-2,4(3H)-dione-hydroxo(trans-l-1,2-diaminocyclohexane)platinum(II) monohydrate, 3-(3-(2-tetrahydrofuryl)propionyl)-6-methyltetrahydropyran-2,4-dione-hydroxo(trans-l-1,2-diaminocyclohexane)-platinum(II) monohydrate, 3-(2-thienylacryloyl)-6-methyl-2H-pyran-2,4(3H)-dione-hydroxo(trans-l-1,2-diaminocyclohexane)platinum(II) hemihydrate, 3-decanoyl-6-methyltetrahydropyran-2,4-dione-hydroxo(trans-l-1,2-diaminocyclohexane)platinum(II), 3-(3-(m-hydroxyphenyl)propionyl)-6-methyl-2H-pyran-2,4(3H)-dione-hydroxo(trans-l-1,2-diaminocyclohexane)platinum(II), 3-(3-(3,4-methylene-dioxyphenyl)propionyl)-6-methyl-2H-pyran-2,4(3H)-dione-hydroxo(-trans-l-1,2-diaminocyclohexane)platinum(II) hemihydrate, 3-acetyl-6-methyl-2H-pyran-2,4(3H)-dione-nitrato(trans-l-1,2-diaminocyclohexane)platinum(II) monohydrate, bis(3-acetyl-6-methyltetrahydropyran-2,4-dione) (trans-l-1,2-diaminocyclohexane)platinum-(II) monohydrate, bis(3-acetyl-6-methyl-2H-pyran-2,4(3H)-dione) (trans-l-1,2-diaminocyclohexane)-platinum(II) monohydrate, bis(3-(3-(2-tetrahydrofuryl)-propionyl)-6-methyltetrahydropyran-2,4-dione) (trans-l-1,2-diaminocyclohexane)platinum(II) monohydrate, hexakis(3-(3-(p-chlorophenyl)propionyl)-6-methyl-2H-pyran-2,4(3H)-dione)tetrahydroxo-pentakis((trans-l-1,2-diaminocyclohexane)platinum(II))tetrahydrate, hexakis(3-(3-(3,4-methylenedioxyphenyl)propionyl)- 6-methyl-2H-pyran-2,4(3H)-dione)-tetrahydroxo-pentakis((trans-l-1,2-diaminocyclohexane)platinum(II)) tetrahydrate, tetrakis(3-(3-(m-hydroxyphenyl)propionyl)-6-methyl-2H-pyran-2,4(3H)-dione)-dihydroxo-tris((trans- 1-1,2-diaminocyclohexane)platinum(II)) dihydrate, and heptakis(3-(3-m-hydroxyphenyl)propionyl)-6-methyl-2H-pyran-2,4(3H)-dione)hydroxotetrakis((trans-l-1,2-diaminocyclohexane)platinum(II)), 3-(3-phenyl)propionyl-6-methyl-2H-pyran-2,4(3H)-dione-hydroxo(trans-l-1,2-diaminocyclohexane)platinum(II) hemihydrate, 3-phenylacetyl-6-methyl-2H-pyran-2,4(3H)-dione-hydroxo(trans-l-1,2-diaminocyclohexane)platinum(II) hemihydrate, 3-(3-(o-methoxyphenyl)propionyl)-6-methyl-2H-pyran-2,4(3H)-dione-hydroxo(trans-l-1,2-diaminocyclohexane)platinum(II) monohydrate, 3-(2-dodecenoil)-6-methyl-2H-pyran-2,4(3H)-dione-hydroxo (trans-l-1,2-diaminocyclohexane)platinum(II), bis(3-(3-(2-furyl)propionyl)-6-methyl-2H-pyran-2,4(3H)-dione) (trans-l-1,2-diaminocyclohexane)-platinum(II) monohydrate, bis(3-(3-(m-hydroxyphenyl)propionyl)-6-methyl-2H-pyran-2,4(3H)-dione) (trans-l-1,2-diaminocyclohexane)platinum(II) monohydrate, bis(3-(3-(m-hydroxyphenyl)propionyl)-6-methyl-2H-pyran-2,4(3H)-dione) (cis-1,2-diaminocyclohexane)-platinum(II) monohydrate, bis(3-(3-(p-chlorophenyl)-propionyl)-6-methyl-2H-pyran-2,4(3H)-dione) (trans-l-1,2-diaminocyclohexane)platinum(II) monohydrate, bis(3-(3-(3,4-methylenedioxyphenyl)propionyl)-6-methyl-2H-pyran-2,4(3H)-dione) (trans-l-1,2-diaminocyclohexane)platinum(II) monohydrate, 3-acetyl-6-methyltetrahydropyran-2,4-dione-hydroxo(trans-d-1,2-diaminocyclohexane)platinum(II) monohydrate, 3-acetyl-6-propyltetrahydropyran-2,4-dione-hydroxo(-trans-l-1,2-diaminocyclohexane)platinum(II) monohydrate, 3-acetyl-6-nonyltetrahydropyran-2,4-dione-hydroxo(trans-l-1,2-diaminocyclohexane)platinum(II), 3-(3-(p-ethoxyphenyl)propionyl)-6-methyl-2H-pyran-2,4(3H)-dione-hydroxo(trans-l-1,2-diaminocyclohexane)platinum(II) monohydrate, 3-acetyl-1-oxaspiro[5,-5]undecane-2,4-dione-hydroxo(trans-l-1,2-diaminocyclohexane)platinum(II) monohydrate, 3-(3-(p-methoxycarbonylphenyl)-6methyl-2H-pyran-2,4(3H)-dione-hydroxo(trans-l-1,2-diaminocyclohexane)platinum(II) monohydrate, 3-(3-(2,2-dimethyl-6-methylcyclohexyl)-propionyl)-6-methyl-2H-pyran-2,4(3H)-dione-hydroxo(trans-l-1,2-diaminocyclohexane)platinum(II), and 3-(5-(p-nitrophenyl)pentanoyl)-6-methyl-2H-pyran-2,4(3H)-dione-hydroxo(trans-l-1,2-diaminocyclohexane)platinum(II) monohydrate.

Especially preferred examples of the compound of the present invention are 3-acetyl-6-methyltetrahydropyran-2,4-dione-hydroxo(trans-l-1,2-diaminocyclohexane)platinum(II) monohydrate, 3-acetyl-6-methyl-2H-pyran-2,4(3H)-dione-hydroxo(trans-l-1,2-diaminocyclohexane)platinum(II) monohydrate, 3-(3-(2-tetrahydrofuryl)propionyl)-6-methyltetrahydropyran-2,4-dione-hydroxo(trans-l-1,2-diaminocyclohexane)-platinum(II) monohydrate, 3-(2-thienylacryloyl)-6-methyl-2H-pyran-2,4(3H)-dione-hydroxo(trans-l-1,2-diaminocyclohexane)platinum(II) hemihydrate, 3-decanoyl-6-methyltetrahydropyran-2,4-dione-hydroxo(trans-l-1,2-diaminocyclohexane)platinum(II), 3-(3-(m-hydroxyphenyl)propionyl)-6-methyl-2H-pyran-2,4(3H)-dione-hydroxo(trans-l-1,2-diaminocyclohexane)platinum(II), 3-(3-(3,4-methylene-dioxyphenyl)propionyl)-6-methyl-2H-pyran-2,4(3H)-dione-hydroxo(-trans-l-1,2-diaminocyclohexane)platinum(II) hemihydrate, 3-acetyl-6-methyl-2H-pyran-2,4(3H)-dione-nitrato(trans-l-1,2-diaminocyclohexane)platinum(II) monohydrate, bis(3-acetyl-6-methyltetrahydropyran-2,4-dione) (trans-l-1,2-diaminocyclohexane)platinum(II) monohydrate, bis(3-acetyl-6-methyl-2H-pyran-2,4(3H)-dione) (trans-l-1,2-diaminocyclohexane)-platinum(II) monohydrate, bis(3-(3-(2-tetrahydrofuryl)-propionyl)-6-methyltetrahydropyran-2,4-dione) (trans-l-1,2-diaminocyclohexane)platinum(II) monohydrate, hexakis(3-(3-(p-chlorophenyl)propionyl)-6-methyl-2H-pyran-2,4(3H)-dione)-tetrahydroxo-pentakis((trans-l-1,2-diaminocyclohexane)platinum(II)) tetrahydrate, hexakis(3-(3-(3,4-methylenedioxyphenyl)propionyl)-6-methyl-2H-pyran-2,4(3H)-dione)tetrahydroxo-pentakis((trans-l-1,2-diaminocyclohexane)platinum(II)) tetrahydrate, tetrakis(3-(3-(m-hydroxyphenyl)propionyl)-6-methyl-2H-pyran-2,4(3H)-dione)dihydroxo-tris((trans-l-1,2-diaminocyclohexane)platinum(II)) dihydrate, and heptakis(3-(3-m-hydroxyphenyl)propionyl)-6-methyl-2H-pyran-2,4(3H)-dione)-hydroxo-tetrakis((trans-l-1,2-diaminocyclohexane)platinum(II)).

The compounds of the present invention with a high anti-tumor activity and a low toxicity are useful for pharmaceutical compositions for the chemotherapy of malignant tumors. Furthermore, some of the platinum complexes of the present invention also exhibit a bacteriocidal activity, and thus are expected to be valuable for use as antimicrobial agents.

For chemotherapeutic use, the pharmaceutical composition comprising a therapeutically effective amount of at least one of the compounds of the present invention in conjunction or admixture with excipients or carriers may be administered in an oral or non-oral manner, preferably as tablets, coated tablets, pills, capsules, powders, troaches, liquid preparations, suppositories or injections. As the excipients or carriers, there can be mentioned lactose, sucrose, glucose, sorbitol, mannitol, potato starch, amilopectin, various other starches, cellulose derivatives such as carboxymethyl cellulose and hydroxyethyl cellulose, gelatin, magnesium stearate, polyvinyl alcohol, calcium stearate, polyethylene glycol wax, gum arabic, talc, titanium dioxide, vegetable oils such as olive oil, peanut oil and sesame oil, paraffin oil, neutral fat base, ethanol, propylene glycol, physiological saline solution, sterilized water, glycerol, a colorant, a taste-improving agent, a stabilizer, an isotonic agent, a buffering agent and other pharmaceutically acceptable excipients or carriers.

The pharmaceutical composition of the present invention contains at least one of the compounds of the present invention in an amount of 0.001 to 85% by weight, preferably 0.005 to 60% by weight, based on the weight of the composition.

Although the dose of the pharmaceutical composition of the present invention depends mainly on the conditions of the disease, the daily dose is generally 0.005 to 200 mg, preferably 0.01 to 50 mg, per kg of the body weight.

The present invention will now be described in detail with reference to the following examples.

REFERENTIAL EXAMPLE 1

3-(2-Dodecenoyl)-6-methyl-2H-pyran-2,4(3H)-dione

To a solution of 30.2 g (0.18 mole) of dehydroacetic acid and 30.0 g (0.19 mole) of decyl aldehyde in 300 ml of chloroform was added dropwise 4.8 g of piperidine at room temperature. The mixture was refluxed for 7 hours, while removing the water formed on the reaction with the aid of a Soxhlet extractor charged with anhydrous sodium sulfate. After the reaction, the reaction mixture was extracted with 600 ml of chloroform. The organic layer was separated, washed with 2N HCl and then with water, and dried over anhydrous sodium sulfate. The extract was concentrated under a reduced pressure and 60 ml of ether/hexane (½) was added to the residue. The mixture was allowed to stand overnight. The precipitated crystal was recovered by filtration and recrystallized from tetrahydrofuran to obtain 9.5 g (yield: 17%) of 3-(2-dodecenoyl)-6-methyl-2H-pyran-2,4(3H)-dione in the form of a white crystal, m.p. 112°–113° C.

¹HNMR(CDCl₃) δ(ppm) 6.03(s,1H), 2.7–2.8(m, 2H), 2.39(s, 3H), 0.9–2.0(m, 19H).

REFERENTIAL EXAMPLE 2

3-(3-(2-Tetrahydrofuryl)propionyl)-6-methyltetrahydropyran-2,4-dione

In 270 ml of tetrahydrofuran was dissolved 32.0 g of 3-(2-furylacryloyl)-6-methyl-2H-pyran-2,4(3H)-dione which had been obtained by condensation between dehydroacetic acid and furfural. To the solution, 1.6 g of 5% palladium on carbon was added as the hydrogenation catalyst. Hydrogenation was carried out at room temperature under a pressure of 5 kg/cm² for 10 hours. The catalyst was removed by filtration and the solvent was evaporated under a reduced pressure. The light-yellow oily product thus obtained was purified by silica gel chromatography to obtain a 21.0 g (yield: 65%) of 3-(3-(2-tetrahydrofuryl)propionyl)-6-methyltetrahydropyran-2,4-dione in the form of the light-yellow crystal, m.p. 43°–45° C.

¹HNMR(CDCl₃) δ(ppm) 4.55(m, 1H), 3.90(m, 1H), 3.80(m, 2H), 3.15(t, 2H), 2.64(d, 2H), 1.8–2.1(m, 6H) 1.45(d, 3H).

REFERENTIAL EXAMPLE 3

3-(2-Thienylacryloyl)-6-methyl-2H-pyran-2,4(3H)-dione

To a solution of 65.0 g (0.39 mole) of dehydroacetic acid and 47.0 g (0.42 mole) of thiophene-2-aldehyde in 370 ml of benzene was added dropwise 6.8 g of piperidine with cooling in an ice-water bath. After termination of the dropwise addition, the mixture was stirred at 50° C. for 7 hours. After the reaction, the solvent was concentrated under a reduced pressure. The precipitated crystal was collected by filtration and recrystallized from toluene to obtain 58.5 g (yield: 58%) of 3-(2-thienylacryloyl)-6-methyl-2H-pyran-2,4(3H)-dione in the form of a light crystal, m.p. 162°–164° C.

¹HNMR(CDCl₃) δ(ppm) 8.07(s, 2H), 7.0–7.5(m, 3H), 5.90(s, 1H), 2.27(s, 3H).

REFERENTIAL EXAMPLE 4

4-Hydroxy-5,6-dihydro-6-methyl-2-pyrone

To a solution of 20.0 g (0.16 mole) of 4-hydroxy-6-methyl-2-pyrone in 250 ml of methanol was added 1.0 g of 5% palladium on carbon as the hydrogenation catalyst. Hydrogenation was carried out at room temperature under a pressure of 20 kg/cm² for 7 hours. The catalyst was removed by filtration and the solvent was removed by evaporation under a reduced pressure. The precipitated crystal was recovered by filtration and recrystallized from ethanol to obtain 14.8 g (yield: 73%) of 4-hydroxy-5,6-dihydro-6-methyl-2-pyrone in the form of a crystal, m.p. 103°–104° C.

¹HNMR(CDCl₃/d₆-DMSO) δ(ppm) 10.7(s, 1H), 5.08(s, 1H), 4.45(m, 1H), 2.35(d, 2H), 1.37(d, 3H).

REFERENTIAL EXAMPLE 5

3-Decanoyl-6-methyltetrahydropyran-2,4-dione

To a solution of 5.13 g (0.040 mole) of 4-hydroxy-5,6-dihydro-6-methyl-2-pyrone and 6.70 g (0.044 mole) of 1,8-diazabicyclo(5,4,0)-undecene (hereinafter referred to as DBU) in 100 ml of toluene was added dropwise 8.39 g (0.044 mole) of decanoyl chloride with stirring and cooling the reaction mixture in an ice-water bath. After termination of the dropwise addition, the mixture was stirred at room temperature for 7 hours. Water was added to the reaction mixture and the mixture was extracted with toluene. The extract was washed with 5% HCl and then with a saturated aqueous solution of sodium chloride, and dried over anhydrous magnesium sulfate. The solvent in the extract was evaporated under a reduced pressure, and the residue was subjected to silica gel column chromatography to purify the product, 4-dodecanoyloxy-6-methyl-5,6-dehydro-2-pyrone. To a solution of 4-dodecanoyloxy-6-methyl-5,6-dihydro-2-pyrone, thus obtained, in 20 ml of toluene was added 0.06 g of 4-pyrolidinopyridine. The mixture was refluxed for 3 hours and the solvent was removed by evaporation under a reduced pressure. The residue was purified by silica gel column chromatography to obtain 1.6 g (yield: 14%) of 3-decanoyl-6-methyltetrahydropyran-2,4-dione, m.p. 62°–63° C.

¹HNMR(CDCl₃) δ(ppm) 17.7(s, 1H), 4.50(m, 1H), 3.02(t, 2H), 2.62(d, 2H), 1.45(d, 3H), 1.0–2.1(m, 14H), 0.98(t, 3H).

REFERENTIAL EXAMPLE 6

3-Phenylacetyl-6-methyl-2H-pyran-2,4(3H)-dione

By adopting the procedure described in Referential Example 5, 3-phenylacetyl-6-methyl-2H-pyran-2,4-dione was prepared from dehydroacetic acid and phenylacetyl chloride. The yield was 34%, m.p. 150°–151° C.

¹HNMR(CDCl₃) δ(ppm) 16.3(s, 1), 7.27(s, 5H), 5.88(s, 1H), 4.40(s, 2H), 2.20(s, 3H).

REFERENTIAL EXAMPLE 7

4-Hydroxy-5,6-dihydro-6-nonyl-2-pyrone

To 4.42 g (0.11 mole) of sodium hydride (60% mineral oil dispersion) was added 250 ml of tetrahydrofuran under a nitrogen atmosphere. To the slurry was added dropwise 11.6 g (0.10 mole) of methyl acetoacetate at 0° C. with stirring. The reaction mixture was stirred for 10 minutes in a nitrogen atmosphere with maintaining the reaction temperature at 0° C. To the reaction mixture was added dropwise 65 ml (0.105 mole) of 1.63M n-butyl lithium in hexane. After stirring the reaction mixture for a further 10 minutes, 17.2 g (0.11 mole) of decyl aldehyde was added to the mixture and the reaction was carried out at −10° C. to 0° C. for 10 minutes. The reaction was terminated by the addition of about 20 ml of concentrated hydrochloric acid. The reaction mixture was worked up by the addition of 100 ml of water and 350 ml of ether. After the organic layer was separated, the aqueous layer was extracted with ether. The ether extracts were combined, washed with an aqueous saturated sodium chloride solution, and dried over anhydrous sodium sulfate. Evaporation of the solvent in the extract under a reduced pressure afforded 22.7 g of an oil. The crude product was purified by silica gel column chromatography to obtain 18.2 g (yield: 67%)

of methyl 5-hydroxy-3-oxotetradecanate. The methyl ester was hydrolyzed in NaOH at room temperature for 2 hours to give a lactone. The reaction mixture was acidified with hydrochloric acid and extracted with ether. The organic layer was separated, washed with an aqueous saturated sodium chloride solution and dried over anhydrous sodium sulfate. The solvent was removed by evaporation under a reduced pressure and the residue was recrystallized from hexane-ethyl acetate to obtain 13.7 g (yield: 85%) of 4-hydroxy-5,6-dihydro-6-nonyl-2-pyrone.

$^1$HNMR(CDCl$_3$) δ(ppm) 4.60(m, 1H), 3.47(d, 2H), 2.60(t, 2H), 1.0–2.1(m, 16H), 0.95(t, 3H).

REFERENTIAL EXAMPLE 8

3-Acetyl-6-nonyltetrahydropyran-2,4-dione

To a solution of 4.5 g (0.019 mole) of 4-hydroxy-5,6-dihydro-6-nonyl-2-pyrone and 3.15 g (0.021 mole) of DBU in 60 ml of toluene was added dropwise. Then, 1.65 g (0.021 mole) of acetyl chloride with cooling in an ice-water bath. The mixture was stirred for 2 hours and water was added to the reaction mixture. The reaction mixture was extracted with toluene and the toluene layer was washed with an aqueous 5% Na$_2$CO$_3$ solution, with 2N-HCl and finally with an aqueous saturated sodium chloride solution, and dried over anhydrous sodium sulfate. The solvent was removed under a reduced pressure to obtain 4.7 g (yield: 89%) of 4-acetoxy-5,6-dihydro-6-nonyl-2-pyrone. The acyloxypyrone was dissolved in 30 ml of toluene and 0.13 g of 4-pyrrolidinopyridine was added to the solution. The mixture was refluxed for 3 hours. The residue obtained by evaporation of the solvent was purified by silica gel column chromatography and recrystallized to obtain 2.4 g (yield: 51%) of 3-acetyl-6-nonyltetrahydropyran-2,4-dione.

$^1$HNMR(CDCl$_3$) δ(ppm) 4.40(m, 1H), 2.68(d, 2H), 2.60(s, 3H), 1.0–2.1(m, 16H), 0.96(t, 3H).

REFERENTIAL EXAMPLE 9

3-Acetyl-6-propyltetrahydropyran-2,4-dione

By adopting the process described in Referential Example 7, 4-hydroxy-5,6-dihydro-6-propyl-2-pyrone was synthesized by using butyl aldehyde in place of decyl aldehyde (overall yield: 23%). Using the propylpyrone thus obtained, 3-acetyl-6-propyltetrahydropyran-2,4-dione was synthesized in a manner similar to that described in Referential Example 8 (yield from the propylpyrone: 41%).

$^1$HNMR(CDCl$_3$) δ(ppm) 17.5(s, 1H), 4.40(m, 1H), 2.65(d, 2H), 2.60(s, 3H), 1.2–2.1(m, 4H), 0.98(t, 3H).

REFERENTIAL EXAMPLE 10

3-Acetyl-1-oxaspiro[5,5]undecane-2,4-dione

By adopting a process similar to that described in Referential Example 7, 4-hydroxy-1-oxaspiro[5,5]undeca-3-ene-2-one was synthesized from cyclohexanone (overall yield: 48%). The spiro-compound thus obtained was used for the synthesis of 3-acetyl-1-oxaspiro[5,5]undecane-2,4-dione in a similar manner to that described in Referential Example 8 (yield from the spiro-compound: 52%).

$^1$HNMR(CDCl$_3$) δ(ppm) 17.5(s, 1H), 2.68(s, 2H), 2.60(s, 3H), 0.9–2.1(m, 10H).

REFERENTIAL EXAMPLE 11

3-(3-(2,2-dimethyl-6-methylcyclohexyl)propionyl)-6-methyl-2H-pyran-2,4(3H)-dione Condensation of 11.0 g (0.065 mole) of dehydroacetic acid with 10.4 g (0.068 mole) of β-cyclocitral was carried out in chloroform by using piperidine as the catalyst to obtain 3-(2,2-dimethyl-6-methyl-1-cyclohexenyl)acryloyl-6-methyl-2H-pyrane-2,4(3H)-dione. This product was hydrogenated in tetrahydrofuran by using 5% palladium on carbon to obtain 2.7 g (yield: 14%) of 3-(3-[2,2-dimethyl-6-methylcyclohexyl propionyl)-6-methyl-]2H-pyrane-2,4(3H)-dione, m.p.100°–102° C.

$^1$HNMR(CDCl$_3$) δ(ppm) 16.7(s, 1H), 5.90(s, 1H), 3.04(t, 2H), 2.22(s, 3H), 1.0–2.1(m, 10H), 0.75–1.0(m, 9H).

EXAMPLE 1

[Pt(trans-l-1,2-diaminocyclohexane)] (3-acetyl-6-methyltetrahydropyran-2,4-dione)(OH).H$_2$O

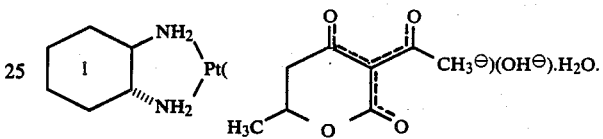

To 100 ml (4.2 millimoles) of an aqueous solution of [Pt(trans-l-dach)(OH)$_2$] ("dach" indicates 1,2-diaminocyclohexane) was added 0.71 g (4.2 millimoles) of 3-acetyl-6-methyltetrahydropyran-2,4-dione. The mixture was stirred at room temperature for 6 hours and thereafter concentrated to dryness at 45° to 50° C. The resulting solid was washed with ethyl acetate and dried at 40° to 45° C. under a reduced pressure to obtain 1.90 g of a yellow complex (yield: 88%).

The melting point, elemental analytical data (Pt content was determined by atomic absorption spectrometry), and IR and NMR data of the obtained complex are as follows.

Melting point: 193° to 197° C. (with decomposition).
Elemental analysis of C$_{14}$H$_{26}$N$_2$O$_6$Pt: Calculated values: C=32.75% H=5.10%, N=5.46%, Pt=37.99%. Found values: C=32.3%, H=4.7%, N=5.3%, Pt=37.6%.

IR(KBr)(cm$^{-1}$) 3400, 3200, 3100, 2940, 2860, 1670, 1610, 1570, 1390, 1290, 1060, 970, 920.

$^1$HNNR(d$_6$-DMSO) δ(ppm) 4.18(m, 1H), 3.58(s, 7H), 2.24(br, 5H), 0.6–2.7(m, 13H).

EXAMPLE 2

[Pt(trans-l-1,2-diaminocyclohexane)] (3-acetyl-6-methyl-2H-pyran-2,4(3H)-dione) (OH).H$_2$O

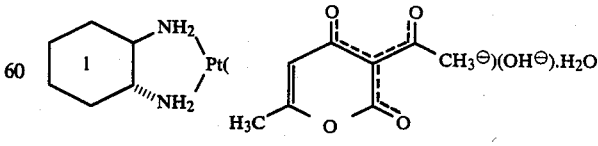

To 100 ml (4.2 millimoles) of an aqueous solution of [Pt(trans-l-dach) (OH)$_2$] was added 0.71 g (4.2 millimoles) of dehydroacetic acid. The reaction and post treatment were carried out in a manner similar to those described in Example 1 to obtain 1.91 g (yield: 89%) of a pinky complex. The melting point, elemental analytical data and IR and NMR spectral data of the so-obtained complex are as follows.

Melting point: 234° to 236° C. (with decomposition).

Elemental analysis of $C_{14}H_{24}H_2O_6Pt$: Calculated values: C=32.88%, H=4.73%, N=5.48%, Pt=38.14%. Found values: C=32.7%, H=4.4%, N=5.4%, Pt=37.3%.

IR(KBr)(cm$^{-1}$) 3400, 3200, 3100, 2940, 2860, 1680, 1660, 1600, 1550, 1400, 1380, 1260, 1160, 1060, 1000.

$^1$HNMR(d$_6$-DMSD) δ(ppm) 5.38(s, 1H), 3.33(s, 5H), 2.25(s, 3H), 0.6–2.6(m, 10H), 1.92(s, 3H).

EXAMPLE 3

[Pt(trans-l-1,2-diaminocyclohexane)]
(3-(3-(2-tetrahydrofuryl)propionyl)-6-methyltetrahydropyran)(OH).(H$_2$O)

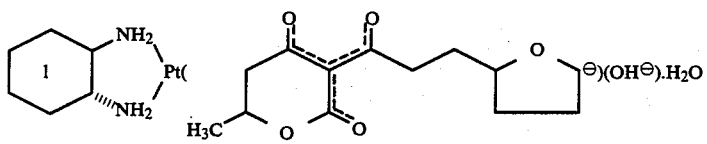

To 100 ml (4.2 millimoles) of an aqueous solution of [Pt(trans-l-dach)(OH)$_2$] was added a solution of 1.07 g (4.2 millimoles) of 3-(2-tetrahydrofuryl)propionyl-6-methyltetrahydropyran-2,4-dione in 10 ml of ethanol. The reaction and the subsequent work up were carried out in a manner similar to those described in Example 1 to obtain 2.38 g of a light-yellow complex (yield: 93%). The melting point, elemental analytical data and IR and NMR spectral data of the so-obtained complex are as follows.

Melting point: 179° to 182° C. (with decomposition).

Elemental analysis of $C_{19}H_{34}N_2O_7Pt$: Calculated values: C=38.19%, H=5.73%, N=4.69%, Pt=32.65%. Found values: C=37.8%, H=5.3%, N=4.6%, Pt=30.0%.

IR(KBr)(cm$^{-1}$) 3400, 3200, 3100, 2940, 2860, 1670, 1610, 1570, 1390, 1340, 1270, 1160, 920.

$^1$HNMR(d$_6$-DMSO) δ(ppm) 4.15(m, 1H), 3.4–3.9(m, 7H), 3.50(s, 5H), 0.5–3.0(m, 21H).

EXAMPLE 4

[Pt(trans-l-1,2-diaminocyclohexane)]
(3-(3-(2-thienyl)acryloyl)-6-methyl-2H-pyran-2,4(3H)-dione)(OH).½H$_2$O

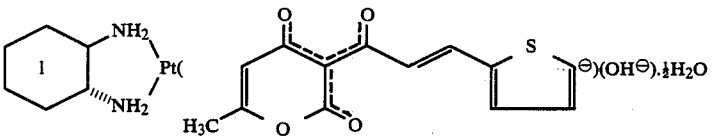

A solution of 1.10 g (4.2 millimoles) of 3-3-(2-thienyl)acryloyl)-6-methyl-2H-pyran-2,4(3H)-dione in 60 ml of ethanol was added to 100 ml (4.2 millimoles) of an aqueous solution of [Pt(trans-l-dach) (H$_2$O)$_2$]. The mixture was stirred at room temperature for 24 hours and then concentrated followed by the removal of a small amount of the resulting insoluble material by filtration. The precipitated crystal was collected by filtration, washed with ethyl acetate and dried at 40° to 45° C. under a reduced pressure to obtain 1.78 g of a brown complex (yield: 71%). The melting point, elemental analytical data and IR and NMR spectral data of the obtained complex are shown below.

Melting point: higher than 300° C.

Elemental analysis of $C_{19}H_{25}N_2SO_{5.5}Pt$: Calculated values: C=38.25%, H=4.22%, N=4.70%, Pt=32.70%. Found values: C=38.0%, H=4.1%, N=4.5%, Pt=31.0%.

IR(KBr) (cm$^{-1}$) 3400, 3200, 3100, 2940, 2860, 1680, 1660, 1620, 1570, 1520, 1400, 1380, 1360, 1250, 1160, 700.

$^1$HNMR(d$_6$-DMSO) δ(ppm) 7.48(s, 2H), 6.8–7.3(m, 3H), 5.50(s, 1H), 3.51(s, 6H), 2.02(s, 3H), 0.6–2.7(m, 10H).

EXAMPLE 5

[Pt(trans-l-1,2-diaminocyclohexane)](3-(3-phenylpropionyl)-6-methyl-2H-pyran-2,4(3H)-dione) (OH).½H$_2$O A solution of 0.54 g (2.1 millimoles) of 3-(3-phenylpropionyl)-6-methyl-2H-pyran-2,4(3H)-dione in 50 ml of ethanol was added to 25 ml (2.1 millimoles) of an aqueous solution of [Pt(trans-l-dach) (OH)$_2$)]. The mixture was stirred at room temperature for 24 hours, filtered to remove a small amount of the resulting insoluble material, and then concentrated to dryness. The precipitated crystal was washed with ethyl acetate and dried at 40° to 45° C. to obtain 1.08 g of a white complex (yield: 87%). The melting point, elemental analytical data and IR and NMR spectral data of the obtained complex are shown below.

Melting point: 227° to 230° C. (with decomposition).

Elemental analysis of $C_{21}H_{29}N_2O_{5.5}Pt$: Calculated values: C=42.57%, H=4.93%, N=4.73%, Pt=32.92%. Found values: C=42.5%, H=4.6%, N=4.4%, Pt=30.6%.

IR(KBr) (cm$^{-1}$) 3400, 3200, 3080, 3030, 2940, 2860, 1730, 1680, 1660, 1600, 1540, 1410, 1260, 1160, 700.

$^1$HNMR(d$_6$-DMSO) δ(ppm) 7.11(s, 5H), 5.92(s, 1H), 5.36(s, 1H), 3.40(s, 7H), 2.6–3.1(m, 4H), 0.5–2.1(m, 1H).

EXAMPLE 6

[Pt(trans-l-1,2-diaminocyclohexane)](3-phenylacetyl-6-methyl-2H-pyran-2,4(3H)-dione) (OH).½H₂O

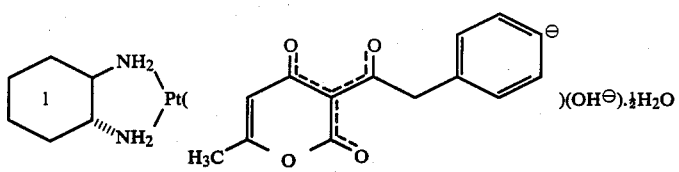

The procedure described in Example 5 was repeated using a solution of 0.51 g (2.1 millimoles) of 3-phenylacetyl-6-methyl-2H-pyran-2,4(3H)-dione in place of 3-(3-phenylpropionyl)-6-methyl-2H-pyran-2,4(3H)-dione to give 1.13 g of a white complex (yield: 93%). The melting point, elemental analytical data and IR spectral data of the obtained complex are as follows.

Melting point: 242° to 247° C. (with decomposition).

Elemental analysis of $C_{20}H_{27}N_2O_{5.5}Pt$: Calculated values: C=41.52%, H=4.70%, N=4.84%, Pt=33.72%. Found values: C=41.5%, H=4.4%, N=4.6%, Pt=31.4%.

IR(KBr) (cm$^{-1}$) 3400, 3180, 3080, 2940, 2860, 1740, 1690, 1660, 1600, 1540, 1510, 1420, 1260, 1160, 720.

EXAMPLE 7

[Pt(trans-l-1,2-diaminocyclohexane)](3-(3-(o-methoxyphenyl)propionyl)-6-methyl-2H-pyran-2,4(3H)-dione) (OH).H₂O

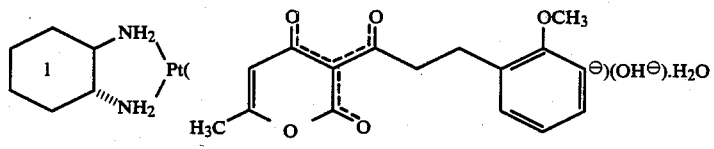

The procedure described in Example 5 was repeated using a solution of 0.61 g (2.1 millimoles) of 3-(3-(o-methoxyphenyl)propionyl-6-methyl-2H-pyran-2,4(3H)-dione in 100 ml of ethanol in place of the solution of 3-(3-phenylpropionyl)-6-methyl-2H-pyrane-2,4(3H)-dione to give 1.30 g of a white complex (yield: 98%). The melting point, elemental analytical data values and IR and NMR spectral data of the obtained complex are as follows.

Melting point: 224° to 227° C. (with decomposition)

Elemental analysis of $C_{22}H_{32}N_2O_7Pt$: Calculated values: C=41.84%, H=5.11%, N=4.44%, Pt=30.89%. Found values: C=41.8%, H=4.8%, N=4.3%, Pt=29.6%.

IR(KBr) (cm$^{-1}$) 3400, 3150, 3070, 2940, 2860, 1720, 1690, 1660, 1600, 1550, 1500, 1460, 1420, 1240, 1160, 1030, 1010, 750.

$^1$HNMR(d₆-DMSO) δ(ppm) 6.7–7.3(m, 4H), 6.00(s, 1H), 5.40(s, 1H), 3.77(s, 3H), 3.47(s, 7H), 2.7–3.1(m, 4H), 0.5–2.7(m, 12H).

EXAMPLE 8

[Pt(trans-l-1,2-diaminocyclohexane)](3-decanoyl-6-methyltetrahydropyran-2,4-dione) (OH)

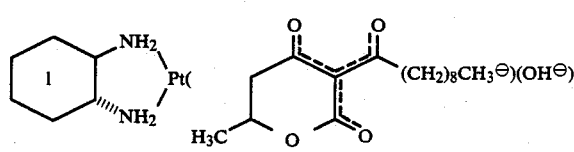

A solution of 0.8 g (2.8 millimoles) of 3-decanoyl-6-methyltetrahydropyran-2,4-dione in 100 ml of ethanol was added to 25 ml (3.2 millimoles) of an aqueous solution of [Pt(trans-l-dach) (OH)₂]. The mixture was stirred at room temperature for 4 days, filtered to remove a small amount of the insoluble material in the reaction mixture by filtration, and concentrated to dryness. The ethanol-soluble fraction of the residue was obtained and evaporated to dryness, washed with ethyl acetate and then with water, and dried at 40° to 45° C. under a reduced pressure to obtain 1.22 g of a light-yellow complex (yield: 72%). The melting point, elemental analytical data and IR and NMR spectral data of the obtained complex are as follows.

Melting point: 175° to 178° C. (with decomposition).

Elemental analysis of $C_{22}H_{40}N_2O_5Pt$: Calculated values: C=43.49%, H=6.63%, N=4.61%, Pt=32.10%. Found values: C=43.5%, H=6.4%, N=4.4%, Pt=30.8%.

IR(KBr) (cm$^{-1}$) 3400, 3200, 3100, 2930, 2860, 1670, 1610, 1570, 1450, 1390, 1260, 1060.

$^1$HNMR(CDCl₃/d₆-DMSO) δ(ppm) 4.20(m, 1H), 3.47(s, 5H), 2.16(d, 2H), 0.6–3.0(m, 32H).

EXAMPLE 9

[Pt(trans-l-1,2-diaminocyclohexane)](3-(2-dodecenoyl)-6-methyl-2H-pyran-2,4(3H)-dione) (OH)

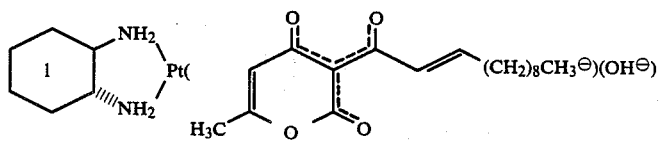

A solution of 1.23 g (4.0 millimoles) of 3-(2-dodecenoyl)-6-methyl-2H-pyran-2,4(3H)-dione in 30 ml of ethanol and 110 ml of methanol was added to 10 ml (4.2 millimoles) of an aqueous solution of [Pt(trans-l-dach) (OH)₂]. The mixture was stirred at room temperature for 24 hours, filtered to remove a small amount of the insoluble material by filtration. The filtrate was concentrated to dryness and washed with ethyl acetate. To the residue was added a solution of 0.25 g (0.8 millimole) of 3-(2-dodecenoyl)-6-methyl-2H-pyran-2,4(3H)-dione in 50 ml of methanol and reaction was carried out at room temperature for 24 hours. The reaction mixture was filtered to remove a small amount of the resulting insoluble material by filtration, concentrated to dryness, and washed with ethyl acetatehexane (1:1) and dried at 40° to 45° C. under a reduced pressure to obtain 1.53 g of a brown complex (yield: 61%). The melting point, elemental analytical data and IR and NMR spectral data of the obtained complex are as follows.

Melting point: 238° to 240° C. (with decomposition).

Elemental analysis of $C_{24}H_{40}N_2O_5Pt$: Calculated values: C=45.64%, H=6.38%, N=4.43%, Pt=30.88%. Found values: C=44.8%, H=6.2%, N=4.2%, Pt=29.0%.

IR(KBr) (cm$^{-1}$) 3430, 3200, 3100, 2930, 2860, 1680, 1660, 1590, 1520, 1450, 1410, 1260, 1170, 1060, 1040.

$^1$HNMR(CDCl$_3$/d$_6$-DMSO) δ(ppm) 5.60(br, 2H), 3.64(br, 5H), 0.5-3.1(m, 33H).

EXAMPLE 10

[Pt(trans-l-1,2-diaminocyclohexane)](3-(3-(m-hydroxyphenyl)propionyl)-6-methyl-2H-pyran-2,4(3H)-dione) (OH)

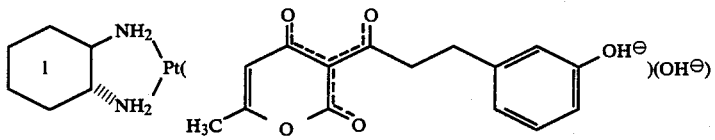

A solution of 1.41 g (5.1 millimoles) of 3-(3-(m-hydroxyphenyl)propionyl)-6-methyl-2H-pyran-2,4(3H)-dione in 25 ml of an aqueous solution of 10.6 millimoles of NaOH was added dropwise to a mixture of 25 ml (5.3 millimoles) of an aqueous solution of [Pt(trans-l-dach) (H$_2$O)$_2$](NO$_3$)$_2$) and 5 ml of ethanol over a period of 25 minutes. The mixture was stirred at room temperature for 2 hours. The precipitated crystal was collected by filtration, washed with ethyl acetate and dried at 40° to 45° C. under a reduced pressure to obtain 1.18 g of a white crystal (yield: 39%). The melting point, elemental analytical data and IR and NMR spectral data of the obtained complex are as follows.

Melting point: 211° to 213° C. (with decomposition).

Elemental analysis of $C_{21}H_{28}N_2O_6Pt$: Calculated values: C=42.07%, H=4.71%, N=4.67%, Pt=32.54%. Found values: C=42.5%, H=4.6%, N=4.4%, Pt=30.6%.

IR(KBr) (cm$^{-1}$) 3400, 3200, 3100, 2940, 2860, 1680, 1660, 1590, 1550, 1410, 1260, 1160, 1060, 1030, 1000, 780.

$^1$HNMR(d$_6$-DMSO) δ(ppm) 7.00(m, 1H), 6.64(br, 3H), 6.00(s, 1H), 5.50(s, 1H), 3.51(br, 5H), 1.98(s, 3H), 0.5-3.2(m, 14H).

EXAMPLE 11

[Pt(trans-l-1,2-diaminocyclohexane)](3-(3-(3,4-methylene-dioxyphenyl)propionyl)-6-methyl-2H-pyran-2,4(3H)-dione) (OH).½H$_2$O

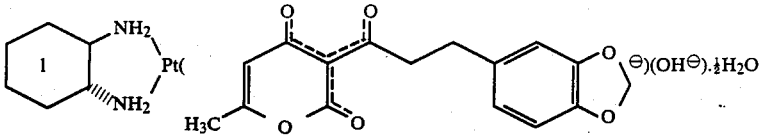

A solution of 1.21 g (4 millimoles) of 3-(3-(3,4-methylene-dioxyphenyl)propionyl)-6-methyl-2H-pyran-2,4(3H)-dione in 8.5 ml of 1N NaOH was added to a mixture of 20 ml (4.2 millimoles) of an aqueous solution of [Pt(trans-l-dach) (H$_2$O)$_2$](NO$_3$)$_2$ and 50 ml of ethanol. The mixture was stirred at room temperature for 4 hours and the reaction mixture was concentrated. The precipitated crystal was collected by filtration, washed with ethyl acetate and dried at 40° to 45° C. under a reduced pressure to obtain 1.52 g of a white complex (yield: 60%). The melting point, elemental analytical data and IR and NMR spectral data of the obtained complex are as follows.

Melting point: 215° to 223° C. (with decomposition).

Elemental analysis of $C_{22}H_{29}N_2O_{7.5}Pt$: Calculated values: C=41.51%, H=4.59%, N=4.40%, Pt=30.65%. Found values: C=41.4%, H=4.3%, N=4.6%, Pt=30.4%.

IR(KBr) (cm$^{-1}$) 3380, 3250, 3200, 3100, 2940, 1730, 1680, 1660, 1610, 1540, 1490, 1420, 1240, 1040, 940.

$^1$HNMR(d$_6$-DMSO) δ(ppm) 6.5-6.8(m, 3H), 5.86(s, 2H), 5.39(s, 1H), 3.40(br, 6H), 1.94(s, 3H), 0.5-3.2(m, 14H).

EXAMPLE 12

[Pt(trans-l-1,2-diaminocyclohexane)](3-acetyl-6-methyl-2H-pyran-2,4(3H)-dione) NO$_3$).H$_2$O

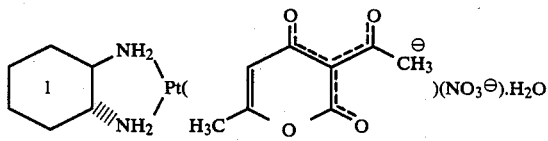

A solution of 2.12 g (12.6 millimoles) of dehydroacetic acid in 12.6 ml of a 1N aqueous solution of NaOH was added dropwise to 30 ml (6.3 millimoles) of an aqueous solution of [Pt(trans-l-dach) (H$_2$O)$_2$](NO$_3$)$_2$ at room temperature with stirring. Reaction was carried out for 20 hours. The precipitated crystal was collected by filtration, washed with water and ethyl acetate and dried at 40° to 45° C. under a reduced pressure to obtain 2.28 g of a white powdery complex (yield: 65%). The melting point, elemental analytical data and IR spectral data of the obtained complex are as follows.

Melting point: 195° to 198° C. (with decomposition).

Elemental analysis of $C_{14}H_{23}N_3O_8Pt$: Calculated values: C=30.22%, H=4.17%, N=7.55%, Pt=35.06%. Found values: C=30.6%, H=3.8%, N=7.4%, Pt=32.8%.

IR(KBr) (cm$^{-1}$) 3440, 3200, 3100, 2940, 2860, 1760, 1730, 1710, 1660, 1550, 1470, 1430, 1380, 1170, 1070, 1030, 1010, 830.

EXAMPLE 13

[Pt(trans-l-1,2-diaminocyclohexane)](3-acetyl-6-methyltetrahydropyran-2,4-dione)$_2$.H$_2$O

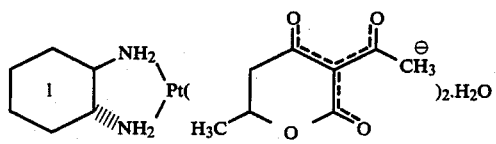

The procedure described in Example 1 was repeated using 1.72 g (10.1 millimoles) of 3-acetyl-6-methyltetrahydropyran-2,4-dione to give 2.40 g of a light-yellow complex (yield: 86%). The melting point, elemental analytical data and IR and NMR spectral data of the obtained complex are as follows.

Melting point: 184° to 188° C. (with decomposition).
Elemental analysis of $C_{22}H_{34}N_2O_9Pt$: Calculated values: C=39.70%, H=5.15%, N=4.21%, Pt=29.31%. Found values: C=39.3%, H=4.9%, N=4.3%, Pt=28.0%.

IR(KBr) (cm$^{-1}$) 3420, 3200, 3080, 2980, 2940, 2860, 1700, 1660, 1620, 1570, 1390, 1290, 1260, 1060, 970, 770.

$^1$HNMR(d$_6$-DMSO) δ(ppm) 4.20(m, 2H), 3.55(s, 6H), 2.1–2.7(m, 10H), 1.5–2.0(m, 6H), 0.5–2.6(m, 10H).

EXAMPLE 14

[Pt(trans-l-1,2-diaminocyclohexane)](3-acetyl-6-methyl-2H-pyran-2,4(3H)-dione)$_2$.H$_2$O

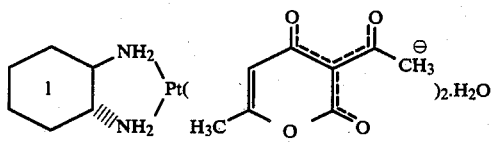

The procedure described in Example 1 was repeated using a solution of 1.71 g (10.1 millimoles) of dehydroacetic acid in 25 ml of ethanol in place of the solution of 3-acetyl-6-methyltetrahydropyran-2,4-dione used in Example 1, to give 2.40 g of a light-yellow complex (yield: 86%). The melting point, elemental analytical data and IR and NMR spectral data of the obtained complex are as follows.

Melting point: 191° to 196° C. (with decomposition).

Elementary analysis values as $C_{22}H_{30}N_2O_9Pt$: Calculated values: C=39.94%, H=4.57%, N=4.23%, Pt=29.49%. Found values: C=39.2%, H=4.4%, N=4.5%, Pt=30.2%.

IR(KBr) (cm$^{-1}$) 3420, 3200, 3080, 2940, 2860, 1730, 1690, 1660, 1600, 1550, 1470, 1400, 1380, 1350, 1280, 1160, 1010.

$^1$HNMR(d$_6$-DMSO) δ(ppm) 5.99(s, 1H), 5.39(s, 1H), 3.48(s, 6H), 2.32(s, 3H), 2.25(s, 3H), 2.05(s, 3H), 1.91(s, 3H), 0.5–2.6(m, 10H).

EXAMPLE 15

[Pt(trans-l-1,2-diaminocyclohexane)](3-(3-(2-tetrahydrofuryl)propionyl-6-methyltetrahydropyran-2,4-dione)$_2$.H$_2$O

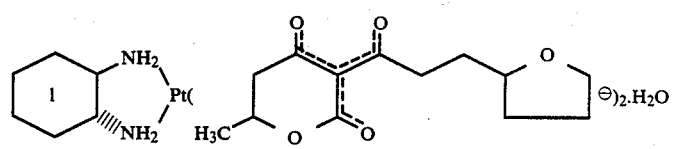

The procedure described in Example 1 was repeated using 2.30 g (9.1 millimoles) of 3-(3-(2-tetrahydrofuryl)-propionyl)-6-methyl-tetrahydropyran-2,4-dione to give 2.80 g of a white complex (yield: 80%). The melting point, elemental analytical data and IR and NMR spectral data of the obtained complex are as follows.

Melting point: 166° to 168° C. (with decomposition).
Elemental analysis of $C_{32}H_{50}N_2O_{11}Pt$: Calculated values: C=46.09%, H=6.04%, N=3.36%, Pt=23.40%. Found values: C=45.7%, H=5.7%, N=3.5%, Pt=24.0%.

IR(KBr) (cm$^{-1}$) 3420, 3150, 3080, 2940, 2860, 1710, 1660, 1560, 1400, 1340, 1260, 1070.

$^1$HNMR(D$_2$O, 400 MHz) δ(ppm) 4.57(m, 1H), 4.50(m, 1H), 3.90(m, 2H), 3.85(m, 2H), 3.75(m, 2H), 2.79(m, 4H), 2.67(d, 1H), 2.52(m, 2H), 2.42(d, 2H), 2.38(m, 1H), 2.10(m, 2H), 2.06(m, 2H), 1.93(m, 4H), 1.78–1.85(m, 4H), 1.63(m, 2H), 1.55(m, 2H), 1.37(m, 2H), 1.39(d, 3H), 1.36(d, 3H), 1.20(m, 2H).

EXAMPLE 16

To 30 ml (3.2 millimoles) of an aqueous solution of Pt(trans-l-dach)SO$_4$ was added 150 ml of a solution of 1.61 g (3.2 millimoles) of 3-(3-(2-tetrahydrofuryl)-propionyl)-6-methyltetrahydropyran-2,4-dione in an aqueous solution of Ba(OH)$_2$. The mixture was stirred at room temperature for 24 hours and concentrated at 45° to 50° C. The precipitate (BaSO$_4$) was removed by filtration under cooling to 10° C. The filtrate was concentrated to dryness, washed with ethyl acetate and dried under a reduced pressure to obtain 1.9 g of a white complex. The IR and NMR spectral data of the obtained complex were substantially in agreement with those of the complex obtained in Example 15. The elemental analytical data were 45.8% of C, 5.8% of H, 3.1% of N, and 22.9% of Pt.

EXAMPLE 17

[Pt(trans-l-1,2-diaminocyclohexane)](3-(3-(2-furyl)propionyl)-6-methyl-2H-pyran-2,4(3H)-dione)$_2$

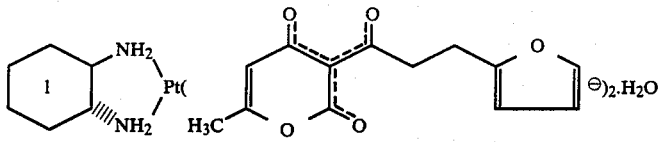

A solution of 1.30 g (5.2 millimoles) of 3-(3-(2-furyl)-propionyl)-6-methyl-2H-pyran-2,4(3H)-dione in a mixed solvent of 10.7 ml of 1N NaOH and 30 ml of ethanol was added to 25 ml (5.3 millimoles) of an aqueous solution of [Pt(trans-l-dach) (H$_2$O)](NO$_3$)$_2$. The mixture was stirred at room temperature for 2 hours. The precipitated crystal was collected by filtration, washed with water and ethyl acetate and dried under a reduced pressure to obtain 0.91 g of a white complex (yield: 21%). The melting point, elemental analytical data and IR spectral data of the obtained complex are as follows.

Melting point: 204° to 207° C. (with decomposition).
Elemental analysis of $C_{32}H_{36}N_2O_{10}Pt$: Calculated values: C=47.82%, H=4.51%, N=3.49%, Pt=24.27%. Found values: C=47.4%, H=4.4%, N=3.5%, Pt=24.9%.

IR(KBr) (cm$^{-1}$) 3420, 3160, 3090, 2940, 2860, 1730, 1680, 1660, 1550, 1420, 1160, 1010, 740.

EXAMPLE 18

[Pt(trans-l-1,2-diaminocyclohexane)](3-(3-(m-hydroxyphenyl)propionyl)-6-methyl-2H-pyran-2,4(3H)-dione)$_2$.H$_2$O

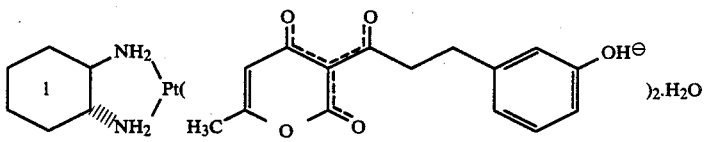

A solution of 1.23 g (4.5 millimoles) of 3-(3-m-hydroxyphenyl)propionyl-6-methyl-2H-pyran-2,4(3H)-dione in 65 ml of methanol, and 4.3 ml of 1N NaOH were added to 20 ml (2.1 millimoles) of an aqueous solution of [Pt(trans-l-dach) (H$_2$O)$_2$](NO$_3$)$_2$. The mixture was stirred at room temperature for 20 hours, concentrated to 38 g and then added dropwise to 75 ml of water to precipitate a thick syrup-like substance. After removal of the supernatant formed, 150 ml of water was added to solidify the syrup-like substance by stirring the mixture at room temperature for 2 hours. The solidified material was recovered by filtration, washed with ethyl acetate and dried under a reduced pressure to obtain 1.20 g of a light-yellow crystal (yield: 65%). The melting point, elemental analytical data and IR spectral data are as follows.

Melting point: 179° to 182° C. (with decomposition).
Elemental analysis of $C_{36}H_{42}N_2O_{11}Pt$: Calculated values: C=49.48%, H=4.84%, N=3.21%, Pt=22.33%. Found values: C=49.8%, H=4.7%, N=3.1%, Pt=21.8%.

IR(KBr) (cm$^{-1}$) 3400, 3200, 3100, 2940, 2860, 1700, 1660, 1590, 1550, 1460, 1420, 1260, 1160, 1010.

EXAMPLE 19

[Pt(cis-1,2-diaminocyclohexane)](3-(3-(m-hydroxyphenyl)propionyl-6-methyl-2H-pyran-2,4(3H)-dione)$_2$.H$_2$O

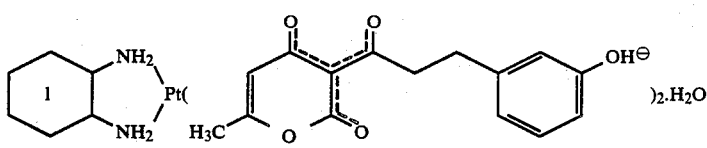

A solution of 2.30 g (8.4 millimoles) of 3-(3-m-hydroxyphenyl)propionyl-6-methyl-2H-pyran-2,4(3H)-dione in a mixed solvent of 8.6 ml of 1N NaOH and 50 ml of water was added to a diluted solution of 20 ml (4.2 millimoles) of an aqueous solution of [Pt(cis-dach)-(H$_2$O)$_2$](NO$_3$)$_2$ with 30 ml of water. The mixture was stirred at room temperature for 2 hours. The precipitated crystal was collected by filtration, washed with water and then with ethyl acetate, and dried under a reduced pressure to obtain 1.80 g of a light-yellow complex (yield: 49%). The melting point, elemental analytical data and IR and NMR spectral data of the obtained complex are as follows.

Melting point: 186° to 190° C. (with decomposition).
Elemental analysis of $C_{36}H_{42}N_2O_{11}Pt$: Calculated values: C=49.48%, H=4.84%, N=3.21%, Pt=22.33%. Found values: C=49.7%, H=4.8%, N=3.2%, Pt=21.9%.

IR(KBr) (cm$^{-1}$) 3400, 3200, 3100, 2940, 2860, 1730, 1690, 1660, 1590, 1550, 1460, 1420, 1250, 1160, 1010, 780.

$^1$HNMR(d$_6$-DMSO) δ(ppm) 9.10(br, 2H), 6.7–7.1(m, 2H), 6.3–6.6(m, 6H), 5.81(s, 1H), 5.32(s, 1H), 3.48(br, 6H), 2.3–3.2(m, 10H), 1.82–2.0(m, 6H), 0.5–1.8(m, 8H).

EXAMPLE 20

[Pt(trans-l-1,2-diaminocyclohexane)](3-(3-(p-chlorophenyl)propionyl-6-methyl-2H-pyran-2,4(3H)-dione)$_2$.-H$_2$O

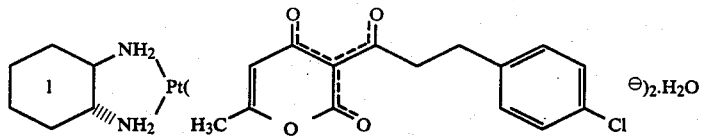

A solution of 2.12 g (7.2 millimoles) of 3-(3-(p-chlorophenyl)propionyl)-6-methyl-2H-pyran-2,4(3H)-dione in 200 ml of methanol was added to 15 ml (3.2 millimoles) of [Pt(trans-l-dach) (H$_2$O)$_2$](NO$_3$)$_2$ and 7.2 ml of 1N NaOH was further added. The mixture was stirred at room temperature for 20 hours, filtered to remove a small amount of the precipitate by filtration, and concentrated to 25 g. The solidified material formed on stirring the mixture at room temperature for 2 hours following the addition of 300 ml of water was recovered by filtration, washed with ethyl acetate and dried under a reduced pressure to obtain 1.75 g of a white complex (yield: 60%). The melting point, elemental analytical data and IR spectral data of the obtained complex are as follows.

Melting point: 188° to 192° C. (with decomposition).
Elemental analysis of C$_{36}$H$_{40}$N$_2$O$_9$Cl$_2$Pt: Calculated values: C=47.48%, H=4.43%, N=3.08%, Pt=21.42%. Found values: C=47.9%, H=4.3%, N=3.2%, Pt=20.8%.

IR(KBr) (cm$^{-1}$) 3420, 3160, 3080, 2940, 2860, 1730, 1690, 1660, 1610, 1550, 1510, 1490, 1420, 1090, 1010, 830.

EXAMPLE 21

[Pt(trans-l-1,2-diaminocyclohexane)](3-(3-(3,4-methylenedioxyphenyl)propionyl-6-methyl-2H-pyran-2,4(3H)-dione)$_2$.H$_2$O

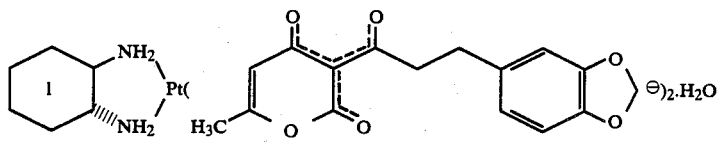

The procedure described in Example 20 was repeated using 2.21 g (7.3 millimoles) of 3-(3-(3,4-methylenedioxyphenyl)propionyl)-6-methyl-2H-pyran-2,4(3H)-dione in place of 3-(3-(p-chlorophenyl)propionyl-6-methyl-1-2H-pyran-2,4(3H)-dione, to afford 2.25 g of a white complex (yield: 76%). The melting point, elemental analytical data and IR spectral data of the obtained complex are as follows.

Melting point: 186° to 188° C. (with decomposition).
Elemental analysis of C$_{38}$H$_{42}$N$_2$O$_{13}$Pt: Calculated values: C=49.09%, H=4.55%, N=3.01%, Pt=20.98%. Found values: C=49.2%, H=4.4%, N=3.2%, Pt=20.8%.

IR(KBr) (cm$^{-1}$) 3420, 3180, 3080, 2940, 1730, 1690, 1660, 1610, 1550, 1500, 1490, 1420, 1400, 1240, 1040, 920.

EXAMPLE 22

[Pt(trans-l-1,2-diaminocyclohexane)]$_5$(3-(3-(p-chlorophenyl)propionyl)-6-methyl-2H-pyran-2,4(3H)-dione)$_6$.(OH)$_4$.4H$_2$O

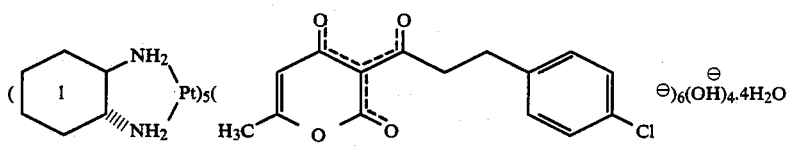

A solution of 1.23 g (4.2 millimoles) of 3-(3-(p-chlorophenyl)propionyl)-6-methyl-2H-pyran-2,4(3H)-dione in a mixed solvent of 4.3 ml of 1N NaOH and 20 ml of water was added dropwise to 25 ml (2.1 millimoles) of an aqueous solution of [Pt(trans-l-dach) (H$_2$O)$_2$](NO$_3$)$_2$ at room temperature. The mixture was stirred for 24 hours. The precipitated crystal was collected by filtration, washed with water and then with ethyl acetate, and dried under a reduced pressure to obtain 1.33 g of a white powdery complex. The melting point, elemental analytical data and IR spectral data of the obtained complex are as follows.

Melting point: 183° to 186° C. (with decomposition).
Elemental analysis of C$_{120}$H$_{154}$N$_{10}$O$_{32}$Cl$_6$Pt$_5$: Calculated values: C=41.94%, H=4.52%, N=4.08%, Cl=6.19%, Pt=28.38%. Found values: C=41.3%, H=4.2%, N=4.0%, Cl=6.0%, Pt=28.0%.

IR(KBr) (cm$^{-1}$) 3360, 3240, 3200, 3080, 2940, 2860, 1670, 1650, 1600, 1540, 1480, 1400, 1370, 1250, 1160, 1000.

EXAMPLE 23

[Pt(trans-l-1,2-diaminocyclohexane)]₅(3-(3-(3,4-methylene-dioxyphenyl)propionyl)-6-methyl-2H-pyran-2,4(3H)-dione)₆(OH)₄.4H₂O

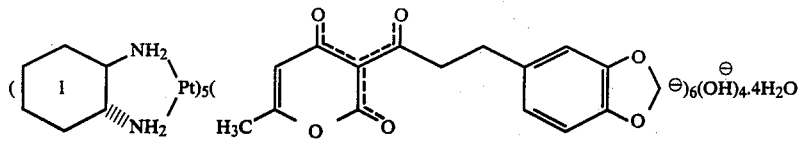

A solution of 1.27 g (4.2 millimoles) of 3-(3-(3,4-methylene-dioxyphenyl)propionyl)-6-methyl-2H-pyran-2,4(3H)-dione in a mixed solvent of 4.3 ml of 1N NaOH and 20 ml of water was added dropwise to 25 ml (2.1 millimoles) of [Pt(trans-l-dach) (H₂O)₂](NO₃)₂ at room temperature and the mixture was stirred for 24 hours. The precipitated crystal was collected by filtration, washed with water and then with ethyl acetate, and dried at 40° C. under a reduced pressure to obtain 1.40 g of a white powdery complex. The melting point, elemental analytical data and IR spectral data of the obtained complex are as follows.

Melting point: 170° to 175° C. (with decomposition).
Elemental analysis of $C_{126}H_{160}N_{10}O_{44}Pt_5$: Calculated values: C=43.31%, H=4.63%, N=4.01%, Pt=27.92%. Found values: C=42.0%, H=4.2%, N=4.1%, Pt=27.3%.

IR(KBr) (cm⁻¹) 3360, 3240, 3200, 3080, 2940, 2860, 1720, 1670, 1640, 1600, 1540, 1480, 1400, 1240, 1030, 930.

EXAMPLE 24

[Pt(trans-l-1,2-diaminocyclohexane)]₃(3-(3-(m-hydroxyphenyl)propionyl)-6-methyl-2H-pyran-2,4(3H)-dione)₄.(OH)₂.2H₂O

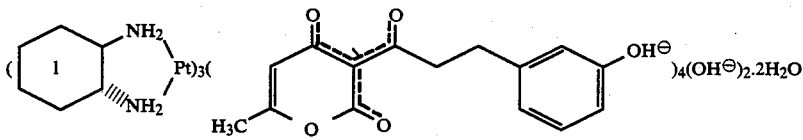

A solution of 1.73 g (6.3 millimoles) of 3-(3-(m-hydroxyphenyl)propionyl)-6-methyl-2H-pyran-2,4(3H)-dione in 30 ml of 0.13N aqueous NaOH was added dropwise to 40 ml (3.2 millimoles) of an aqueous solution of [Pt(trans-l-dach) (H₂O)₂](NO₃)₂ at room temperature while stirring. The mixture was stirred for 2 hours. The precipitated crystal was collected by filtration, washed with water and then with ethyl acetate to remove the unreacted starting materials, and dried at 40° C. under a reduced pressure to obtain 1.60 g of a white powdery complex. The melting point and elemental analytical data of the obtained complex are as follows.

Melting point: 200° to 204° C. (with decomposition).
Elemental analysis of $C_{78}H_{100}N_6O_{24}Pt_3$: Calculated values: C=44.81%, H=4.82%, N=4.02%, Pt=27.99%. Found values: C=44.5%, H=4.8%, N=3.9%, Pt=27.3%.

EXAMPLE 25

[Pt(trans-l-1,2-diaminocyclohexane)]₄(3-(3-(m-hydroxyphenyl)propionyl)-6-methyl-2H-pyran-2,4(3H)-dione)₇.(OH)

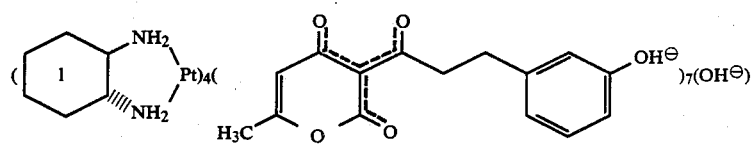

A solution of 0.58 g (2.1 millimoles) of 3-(3-(m-hydroxyphenyl)propionyl)-6-methyl-2H-pyran-2,4(3H)-dione in 17 ml of 0.13N aqueous NaOH was added dropwise to 35 ml (1.05 millimoles) of an aqueous solution of [Pt(trans-l-dach) (H₂O)₂](NO₃)₂ over a period of about 30 minutes, and the mixture was stirred at room temperature for 3 days. The precipitated crystal was collected by filtration, washed with water and then with ethyl acetate, and dried under a reduced pressure to obtain 0.50 g of a white powdery complex. The melting point, elemental analytical data and IR spectral data of the obtained complex are as follows.

Melting point: 171° to 174° C. (with decomposition).
Elemental analysis of $C_{129}H_{148}N_8O_{36}Pt_4$: Calculated values: C=48.92%, H=4.71%, N=3.54%, Pt=24.64%. Found values: C=47.6%, H=4.7%, N=3.4%, Pt=23.3%.

IR(KBr) (cm⁻¹) 3400, 3200, 3100, 2940, 2860, 1680, 1650, 1580, 1540, 1450, 1410, 1250, 1160, 1000, 780.

EXAMPLE 26

[Pt(trans-d-1,2-diaminocyclohexane)](3-acetyl-6-methyltetrahydropyran-2,4-dione) (OH).H₂O

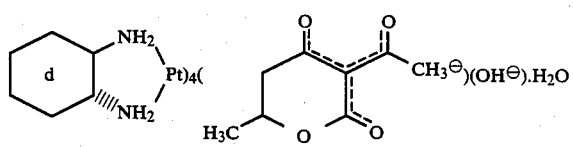

The procedure described in Example 1 was repeated using an aqueous solution of [Pt(trans-d-dach) (OH)₂] in place of the aqueous solution of [Pt(trans-l-dach) (OH)₂] used in Example 1, to give 1.90 g of a complex (yield: 88%). The melting point, elemental analytical data and IR and NMR spectral data of the obtained complex are as follows.

Melting point: 231° to 233° C. (with decomposition) (blackened at 227° C.).

Elemental analysis of $C_{14}H_{26}N_2O_6Pt$: Calculated values: C=32.75%, H=5.10%, N=5.46%, Pt=37.99%. Found values: C=33.2%, H=4.7%, N=5.3%, Pt=36.3%.

IR(KBr) (cm$^{-1}$) 3400, 3200, 3100, 2940, 2860, 1670, 1610, 1570, 1390, 1290, 1060, 970, 920.

$^1$HNMR(d$_6$-DMSO) δ(ppm) 4.20(m, 1H), 3.57(s, 7H), 2.23(br, 5H), 0.6-2.7 (m, 13H).

EXAMPLE 27

[Pt(trans-l-1,2-diaminocyclohexane)](3-acetyl-6-propyl-tetrahydropyran-2,4-dione) (OH).H$_2$O

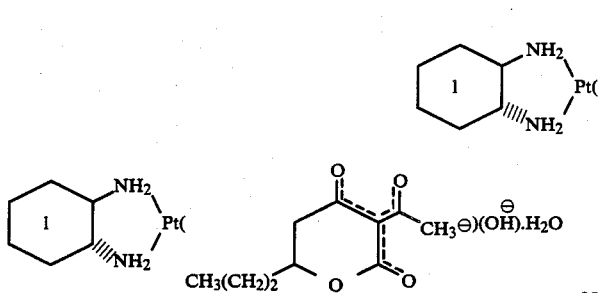

A solution of 0.84 g (4.2 millimoles) of 3-acetyl-6-propyltetrahydropyran-2,4-dione in 70 ml of ethanol was added to 50 ml (4.2 millimoles) of an aqueous solution of [Pt(trans-l-dach)(OH)$_2$]. The reaction mixture was stirred at room temperature for 24 hours and concentrated at 45° to 50° C. under a reduced pressure to dryness. The resulting solid was washed with ethyl acetate and dried under a reduced pressure to obtain 1.88 g (yield: 83%) of a pale yellow crystalline complex. The melting point, elemental analytical data and IR and NMR spectral data of the obtained complex are as follows.

Melting point: 228° to 230° C. (with decomposition).

Elemental analysis of $C_{16}H_{30}N_2O_6Pt$: Calculated values: C=35.49%, H=5.58%, N=5.17%, Pt=36.03%. Found values: C=35.7%, H=5.2%, N=5.1%, Pt=34.5%.

IR(KBr) (cm$^{-1}$) 3400, 3200, 3100, 2940, 2860, 1670, 1610, 1570, 1390, 1280, 1060, 1040.

$^1$HNMR(d$_6$-DMSO) δ(ppm) 4.10(m, 1H), 3.51(s, 6H), 2.0-2.7(m, 7H), 0.5-2.0(m, 16H).

EXAMPLE 28

[Pt(trans-l-1,2-diaminocyclohexane)](3-acetylnonyltetrahydropyran-2,4-dione)(OH)

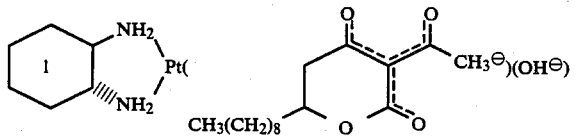

The procedure described in Example 27 was repeated wherein a solution of 1.15 g (4.1 millimoles) of 3-acetylnonyltetrahydropyran-2,4-dione in 260 ml of ethanol was added to 50 ml (4.2 millimoles) of an aqueous solution [Pt(trans-l-dach) (OH)$_2$]. The reaction mixture, was processed as described in Example 27 to obtain 1.69 g of a complex (yield: 68%). The melting point, elemental analytical data and IR and NMR spectral data of the obtained complex are as follows.

Melting point: higher than 300° C.

Elemental analysis of $C_{22}H_{40}N_2O_5Pt$: Calculated values: C=43.49%, H=6.63%, N=4.61%, Pt=32.10%. Found values: C=43.3%, H=6.5%, N=4.5%, Pt=30.4%.

IR(KBr) (cm$^{-1}$) 3400, 3200, 3100, 2940, 2860, 1670, 1610, 1570, 1390, 1290, 1060.

$^1$HNMR(CDCl$_3$/d$_6$-DMSO) δ(ppm) 4.10(m, 1H), 3.65(br, 5H), 2.39(m, 7H), 0.5-2.0(m, 27H).

EXAMPLE 29

[Pt(trans-l-1,2-diaminocyclohexane)](3-(3-(p-ethoxyphenyl)propionyl)-6-methyl-2H-pyran-2,4(3H)-dione)-(OH).H$_2$O

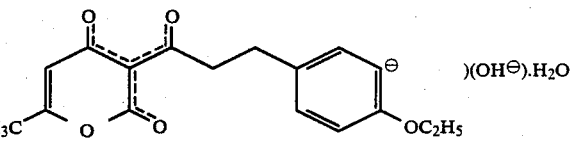

The procedure described in Example 27 was repeated wherein a solution of 0.31 g of 3-(3-(p-ethoxyphenyl)-propionyl)-6-methyl-2H-pyran-2,4(3H)-dione in 200 ml of ethanol was added to 12.5 ml (1.05 millimoles) of an aqueous solution [Pt(trans-l-dach)(OH)$_2$]. The reaction mixture was processed as described in Example 27 to obtain 0.46 g of a complex (yield: 68%). The melting point, elemental analytical data and IR spectral data of the obtained complex are as follows.

Melting point: 186° to 192° C. (with decomposition) (blackened at 180° C.).

Elemental analysis of $C_{23}H_{34}N_2O_7Pt$: Calculated values: C=42.86%, H=5.32%, N=4.35%, Pt=30.26%. Found values: C=42.9%, H=5.0%, N=4.3%, Pt=29.4%.

IR(KBr) (cm$^{-1}$) 3420, 3200, 3100, 2940, 2860, 1730, 1690, 1660, 1620, 1550, 1510, 1410, 1240, 1180, 1050, 840.

EXAMPLE 30

[Pt(trans-l-1,2-diaminocyclohexane)](3-acetyl-1-oxaspiro [5,5]-undecane-2,4-dione)(OH).H$_2$O

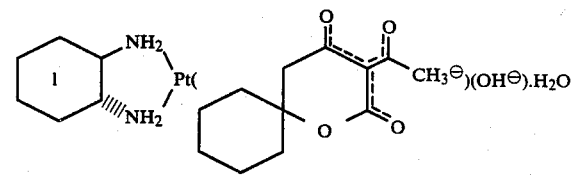

The procedure described in Example 27 was repeated using a solution of 0.94 g (4.2 millimoles) of 3-acetyl-1-oxaspiro[5,5']undecane-2,4-dione in 70 ml of ethanol with 50 ml (4.2 millimones) of an aqueous solution [Pt(trans-l-dach)(OH)$_2$] to give 1.95 g of a complex (yield: 82%). The melting point, elemental analytical data and IR and NMR spectral data of the obtained complex are as follows.

Melting point: 199° to 201° C.

Elemental analysis of $C_{18}H_{32}N_2O_6Pt$: Calculated values: C=38.09%, H=5.68%, N=4.94%, Pt=34.37%. Found values: C=38.2%, H=5.3%, N=4.9%, Pt=32.9%.

IR(KBr) (cm$^{-1}$) 3400, 3200, 3100, 2940, 2860, 1670, 1610, 1570, 1450, 1390, 1180, 1060, 1040.

$^1$HNMR(d$_6$-DMSO) δ(ppm) 3.50(br, 7H), 2.60(m, 2H), 2.48(m, 5H), 0.5-2.1(m, 18H).

EXAMPLE 31

[Pt(trans-l-1,2-diaminocyclohexane)](3-(3-(p-methoxycarbonylphenyl)propionyl)-6-methyl-2H-pyran-2,4(3H)-dione)(OH)

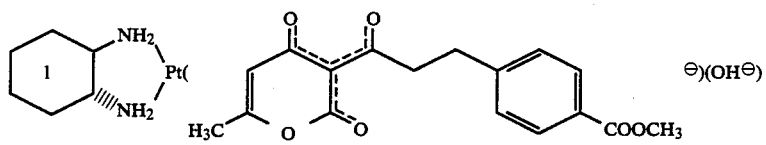

The procedure described in Example 27 was repeated using a solution of 0.66 g (2.1 millimoles) of 3-(3-(p-methoxycarbonylphenyl)propionyl)-6-methyl-2H-pyran-2,4(3H)-dione in 200 ml of ethanol with 25 ml (2.1 millimoles) of an aqueous solution [Pt(trans-l-dach)(OH)$_2$] to give 1.03 g of a complex (yield: 76%). The melting point, elemental analytical data and IR and NMR spectral data of the obtained complex are as follows.

Melting point: 183° to 190° C. (with decomposition).

Elemental analysis of $C_{23}H_{30}N_2O_7Pt$: Calculated values: C=43.06%, H=4.71%, N=4.37%, Pt=30.41%. Found values: C=42.1%, H=4.7%, N=4.2%, Pt=28.9%.

IR(KBr) (cm$^{-1}$) 3420, 3200, 3100, 2940, 2860, 1720, 1700, 1660, 1610, 1550, 1410, 1280, 1180, 1110, 840.

$^1$HNMR(d$_6$-DMSO) δ(ppm) 7.7-8.0(m, 2H), 7.2-7.5(m, 2H), 5.43(s, 1H), 3.82(s, 3H), 3.50(br, 5H), 2.97(m, 4H), 0.5-2.7(m, 13H).

EXAMPLE 32

[Pt(trans-l-1,2-diaminocyclohexane)](3-(3-(2,2-dimethyl-6-methylcyclohexyl)propionyl)-6-methyl-2H-pyran-2,4(3H)-dione)(OH)

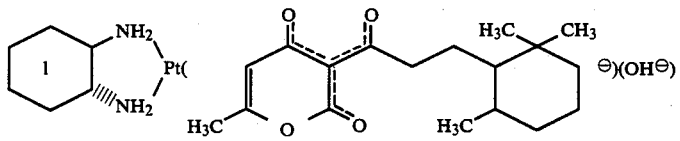

The procedure described in Example 27 was repeated using a solution of 0.65 g (2.1 millimoles) of 3-(3-(2,2-dimethyl-6-methylcyclohexyl)propionyl)-6-methyl-2H-pyran-2,4(3H)-dione in 80 ml of ethanol with 25 ml (2.1 millimoles) of an aqueous solution of [Pt(trans-l-dach)(OH)$_2$] to give 1.16 g of a complex (yield: 87%). The melting point, elemental analytical data and IR spectral data of the obtained complex are as follows.

Melting point: 215° to 220° C. (with decomposition).

Elemental analysis of $C_{24}H_{40}N_2O_5Pt$: Calculated values: C=45.64%, H=6.38%, N=4.43%, Pt=30.88%. Found values: C=45.3%, H=6.2%, N=4.1%, Pt=28.3%.

IR(KBr) (cm$^{-1}$) 3420, 3160, 3070, 2940, 2860, 1730, 1680, 1660, 1600, 1550, 1500, 1420.

EXAMPLE 33

[Pt(trans-l-1,2-diaminocyclohexane)](3-(5-(p-nitrophenyl)pentanoyl)6-methyl-2H-pyran-2,4(3H)-dione)-(OH).H$_2$O

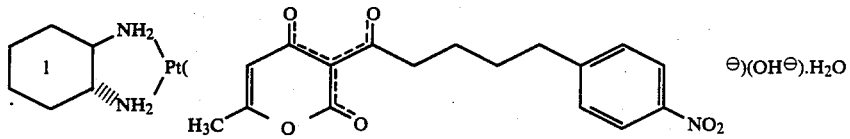

The procedure described in Example 27 was repeated using a solution of 0.35 g (1.05 millimoles) of 3-(5-(p-nitrophenyl)pentanoyl)-6-methyl-2H-pyran-2,4(3H)-dione in 180 ml of ethanol with 12.5 ml (1.05 millimoles) of an aqueous solution of [Pt(trans-l-dach)(OH)$_2$] to give 0.53 g of a complex (yield: 75%). The melting point, elemental analytical data and IR and NMR spectral data of the obtained complex are as follows.

Melting point: 180°-188° C. (with decomposition) (blackened at 175° C.).

Elemental analysis of $C_{23}H_{33}N_3O_8Pt$: Calculated values: C=40.95%, H=4.93%, N=6.23%, Pt=28.92%. Found values: C=40.4%, H=4.5%, N=6.8%, Pt=27.8%.

IR(KBr) (cm$^{-1}$) 3420, 3200, 3100, 2940, 2860, 1680, 1660, 1600, 1540, 1520, 1410, 1340, 840.

$^1$HNMR(d$_6$-DMSO) δ(ppm) 8.0-8.3(m, 2H), 7.3-7.6(m, 2H), 5.47(s, 1H), 3.54(br, 7H), 2.5-3.0(m, 4H), 0.5-2.4(m, 17H).

EXAMPLE 34

Approximately 10$^5$ cells of mouse leukemia L1210 which had been subcultured in DBA/2 mouse were inoculated into the abdominal cavity of CDF$_1$ mouse (male, 8 weeks old, each group consisting of 10 mice). A test platium complex was administered intraperitoneally three times, that is, once a Day 1, on Day 5 and on Day 9, being the day of the inoculation Day 0. CBDCA and CDDP were tested as the positive controls. Each complex tested was used in the form of a solution or suspension in 0.05% "Tween 80" in saline. Anti-tumor activity was evaluated based on the index, T/C value, calculated according to the following formula:

$$T/C\ (\%) = \frac{\text{average survival days of treated animals}}{\text{average survival days of control animals}} \times 100$$

as well as on the number of living mice on the 30th day. The results are shown in Table 1.

TABLE 1

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.4 ± 0.5 | — | 0/10 |
| Compound of Example 24 | 1 | 10.1 ± 0.3 | 120 | 0/10 |
|  | 5 | 14.0 ± 3.1 | 167 | 0/10 |
|  | 10 | 27.6 ± 5.5 | 329 | 6/10 |
|  | 25 | 27.2 ± 4.6 | 324 | 6/10 |
|  | 50 | 9.5 ± 0.7 | 113 | 0/10 |
|  | 100 | 6.0 | 71 | 0/10 |
|  | 200 | 5.5 ± 2.1 | 66 | 0/10 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |
| Control | — | 8.5 ± 0.7 | — | 0/10 |
| CDDP | 5.0 | 21.7 ± 5.5 | 255 | 1/10 |
|  | 7.5 | 23.0 ± 5.0 | 270 | 3/10 |
|  | 10.0 | 14.5 ± 3.8 | 171 | 0/10 |

EXAMPLE 35

Using mouse leukemia L1210 as the tester cell line, anti-tumor activity of the compounds of the present invention was examined in the same manner as described in Example 34 with the exception of the use of CDF₁ mouse (male, 6 weeks old, each group consisting of 6 to 10 mice).

The results are shown in Tables 2 through 9.

TABLE 2

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.3 ± 0.9 | — | 0/10 |
| Compound of Example 15 | 1 | 8.5 ± 0.8 | 102 | 0/6 |
|  | 10 | 10.3 ± 2.7 | 124 | 0/6 |
|  | 25 | 12.8 ± 3.1 | 154 | 0/6 |
|  | 50 | 19.8 ± 7.5 | 239 | 1/6 |
|  | 100 | 26.0 ± 3.2 | 313 | 2/6 |
|  | 200 | 18.2 ± 8.9 | 219 | 1/6 |
| CDDP | 2.5 | 14.8 ± 2.3 | 178 | 0/6 |
|  | 5 | 20.7 ± 5.1 | 249 | 0/6 |
|  | 7.5 | 20.0 ± 5.2 | 241 | 1/6 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |

TABLE 3

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.4 ± 1.0 | — | 0/10 |
| Compound of Example 12 | 1 | 8.2 ± 0.4 | 98 | 0/6 |
|  | 10 | 11.3 ± 0.8 | 135 | 0/6 |
|  | 25 | 19.0 ± 8.5 | 226 | 2/6 |
|  | 50 | 18.0 ± 6.2 | 214 | 1/6 |
|  | 100 | 9.5 ± 1.2 | 113 | 0/6 |
|  | 200 | 5.0 | 60 | 0/6 |
| CDDP | 2.5 | 10.5 ± 1.8 | 125 | 0/6 |
|  | 5.0 | 15.5 ± 1.4 | 185 | 0/6 |
|  | 7.5 | 22.3 ± 3.9 | 266 | 1/6 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |

TABLE 4

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.3 ± 0.7 | — | 0/10 |
| Compound of Example 22 | 1 | 9.5 ± 1.0 | 114 | 0/6 |
|  | 10 | 19.8 ± 5.8 | 239 | 1/6 |
|  | 25 | 25.5 ± 4.9 | 307 | 3/6 |
|  | 50 | 9.1 ± 0.4 | 110 | 0/6 |
|  | 100 | 3.7 ± 3.1 | 43 | 0/6 |
|  | 200 | 1.0 | 12 | 0/6 |
| CDDP | 2.5 | 14.7 ± 1.5 | 177 | 0/6 |
|  | 5.0 | 19.5 ± 4.3 | 235 | 0/6 |
|  | 7.5 | 21.2 ± 5.4 | 260 | 1/6 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |

TABLE 5

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.3 ± 0.7 | — | 0/10 |
| Compound of Example 23 | 1 | 11.0 ± 3.3 | 133 | 0/6 |
|  | 10 | 24.8 ± 5.6 | 299 | 2/6 |
|  | 25 | 22.8 ± 6.0 | 275 | 1/6 |
|  | 50 | 7.8 ± 2.4 | 94 | 0/6 |
|  | 100 | 4.5 ± 1.8 | 54 | 0/6 |
|  | 200 | 1.3 ± 0.8 | 16 | 0/6 |
| CDDP | 2.5 | 14.7 ± 1.5 | 177 | 0/6 |
|  | 5.0 | 19.5 ± 4.3 | 235 | 0/6 |
|  | 7.5 | 21.2 ± 5.4 | 260 | 1/6 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |

TABLE 6

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.4 ± 1.0 | — | 0/10 |
| Compound of Example 25 | 1 | 9.0 ± 1.1 | 107 | 0/6 |
|  | 10 | 20.7 ± 5.5 | 246 | 1/6 |
|  | 25 | 27.7 ± 5.7 | 330 | 5/6 |
|  | 50 | 15.0 ± 8.7 | 179 | 1/6 |
|  | 100 | 4.8 ± 2.7 | 57 | 0/6 |
|  | 200 | 2.7 ± 1.5 | 24 | 0/6 |
| CDDP | 2.5 | 10.5 ± 1.8 | 125 | 0/6 |
|  | 5 | 15.5 ± 1.4 | 185 | 0/6 |
|  | 7.5 | 22.3 ± 3.9 | 266 | 1/6 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |

TABLE 7

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.4 ± 1.0 |  | 0/10 |
| Compound of Example 1 | 1 | 9.8 ± 1.5 | 117 | 0/6 |
|  | 10 | 28.0 ± 4.9 | 333 | 5/6 |
|  | 25 | 9.7 ± 3.2 | 115 | 0/6 |
|  | 50 | 4.5 ± 1.0 | 54 | 0/6 |
|  | 100 | 1.7 ± 1.6 | 20 | 0/6 |
|  | 200 | 1.0 | 12 | 0/6 |
| Compound of Example 2 | 1 | 9.3 ± 0.5 | 111 | 0/6 |
|  | 10 | 24.8 ± 5.5 | 295 | 2/6 |
|  | 25 | 19.2 ± 7.4 | 229 | 1/6 |
|  | 50 | 7.3 ± 2.6 | 87 | 0/6 |
|  | 100 | 3.5 ± 2.0 | 42 | 0/6 |
|  | 200 | 1.0 | 12 | 0/6 |
| Compound of Example 13 | 1 | 8.5 ± 0.5 | 101 | 0/6 |
|  | 10 | 11.5 ± 1.2 | 137 | 0/6 |
|  | 25 | 14.2 ± 3.2 | 169 | 0/6 |
|  | 50 | 17.0 ± 3.0 | 202 | 0/6 |
|  | 100 | 15.5 ± 5.0 | 185 | 0/6 |
|  | 200 | 6.0 | 71 | 0/6 |
| Compound of Example 14 | 1 | 8.7 ± 0.5 | 104 | 0/6 |
|  | 10 | 13.8 ± 3.6 | 164 | 0/6 |
|  | 25 | 19.7 ± 7.5 | 235 | 1/6 |
|  | 50 | 10.0 ± 1.1 | 119 | 0/6 |
|  | 100 | 6.3 ± 2.0 | 75 | 0/6 |
|  | 200 | 2.8 ± 1.6 | 33 | 0/6 |

TABLE 8

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.5 ± 0.7 |  | 0/10 |
| Compound of Example 3 | 1 | 9.2 ± 0.4 | 108 | 0/6 |
|  | 10 | 17.3 ± 6.1 | 204 | 0/6 |
|  | 25 | 26.5 ± 3.9 | 312 | 3/6 |
|  | 50 | 8.3 ± 1.4 | 98 | 0/6 |
|  | 100 | 3.7 ± 1.5 | 44 | 0/6 |
|  | 200 | 2.8 ± 1.6 | 33 | 0/6 |
| Compound of Example 10 | 1 | 10.0 ± 1.1 | 118 | 0/6 |
|  | 10 | 24.3 ± 7.1 | 286 | 3/6 |
|  | 25 | 24.7 ± 5.9 | 291 | 3/6 |
|  | 50 | 10.8 ± 5.4 | 127 | 0/6 |
|  | 100 | 3.3 ± 0.5 | 39 | 0/6 |
|  | 200 | 2.0 | 24 | 0/6 |
| Compound of Example 11 | 1 | 8.8 ± 0.4 | 104 | 0/6 |
|  | 10 | 14.2 ± 6.1 | 167 | 0/6 |
|  | 25 | 25.8 ± 3.4 | 304 | 1/6 |
|  | 50 | 20.0 ± 9.4 | 235 | 2/6 |
|  | 100 | 5.7 ± 1.9 | 67 | 0/6 |
|  | 200 | 3.0 ± 1.7 | 35 | 0/6 |

TABLE 9

Anti-tumor Activity of Platinum Complexes towards Mouse Leukemia L1210 in Mice

| Compound | Dose (mg/kg) | Survival days (mean ± standard deviation) | T/C (%) | Survival rate |
|---|---|---|---|---|
| Control | — | 8.1 ± 0.3 | 100 | 0/10 |
| Compound of Example 4 | 1 | 9.7 ± 1.2 | 120 | 0/6 |
|  | 10 | 26.3 ± 6.0 | 325 | 2/6 |
|  | 25 | 11.7 ± 1.4 | 144 | 0/6 |
|  | 50 | 3.8 ± 0.4 | 47 | 0/6 |
|  | 100 | 2.0 ± 0.6 | 25 | 0/6 |
|  | 200 | 1.0 | 12 | 0/6 |
| Control | — | 8.1 ± 0.9 | 100 | 0/10 |
| Compound of Example 8 | 1 | 9.0 ± 2.0 | 111 | 0/6 |
|  | 10 | 11.7 ± 1.8 | 144 | 0/6 |
|  | 25 | 22.7 ± 8.9 | 280 | 3/6 |
|  | 50 | 26.3 ± 4.7 | 325 | 2/6 |
|  | 100 | 23.0 ± 10.1 | 284 | 2/6 |
|  | 200 | 6.5 ± 0.8 | 80 | 0/6 |

EXAMPLE 36

The acute toxicity of the compound of Example 24 to mice was assessed by intraperitoneal administration to $CDF_1$ mice (male, 6 weeks old, 10 mice/group). CBDCA and CDDP were used as the controls. Each medicine was used in the state dissolved or suspended in a 0.05% solution of "Tween 80". The $LD_{50}$ value was calculated from the death rate on the 14th day from the date of the administration according to the Litchfield-Wilcoxon method. The results are shown in Table 10.

TABLE 10

Results of Acute Toxicity Test of Platinum Complex

| Compound | $LD_{50}$ Value (mg/kg) |
|---|---|
| Compound of Example 24 | Larger than 200 |
| CBDCA | 140 |
| CDDP | 23 |

EXAMPLE 37

The acute toxicity test of the compounds of the present invention to mice were carried out by using CDDP as the control. Platinum complexes to be tested was administered intraperitoneally to Slc:ICR mice (male, 5 weeks old, 6 mice/group). Each complex was used in the form of a solution or suspension in a 0.05% "Tween 80" in saline. The $LD_{50}$ value was calculated by the Miller-Tainter method from the death rate on the 14th day from the date of the administration. The results are shown in Table 11.

TABLE 11

| Compound | $LD_{50}$ Value (mg/kg) |
|---|---|
| CDDP | 15.3 |
| Compound of Example 1 | 18 |
| Compound of Example 2 | 18 |
| Compound of Example 3 | 35 |

TABLE 11-continued

| Compound | LD$_{50}$ Value (mg/kg) |
| --- | --- |
| Compound of Example 4 | 35 |
| Compound of Example 8 | 122 |
| Compound of Example 10 | 35 |
| Compound of Example 11 | 41 |
| Compound of Example 12 | 73 |
| Compound of Example 13 | 98 |
| Compound of Example 14 | 61 |
| Compound of Example 15 | >200 |
| Compound of Example 17 | >200 |
| Compound of Example 18 | 180 |
| Compound of Example 19 | 98 |
| Compound of Example 20 | 165 |
| Compound of Example 21 | 107 |
| Compound of Example 22 | 61 |
| Compound of Example 23 | 45 |
| Compound of Example 25 | 85 |

EXAMPLE 38

The compound of the present invention was dissolved in a physiological saline solution and the antimicrobial activity to *E. coli* WP2uvrA was measured according to the method of Ishizawa et al. Japan J. Pharmacol., 31, 883–889 (1981). The results are shown in Table 12.

TABLE 12

| Compound | SD$_{50}$ Value (μM) |
| --- | --- |
| Compound of Example 1 | 36 |
| Compound of Example 2 | 84 |
| Compound of Example 3 | 46 |
| Compound of Example 4 | 39 |
| Compound of Example 10 | 24 |
| Compound of Example 11 | 17 |
| Compound of Example 13 | 228 |
| Compound of Example 14 | 76 |
| Compound of Example 19 | 106 |

We claim:

1. A platinum (II) complex represented by the following general formula (A):

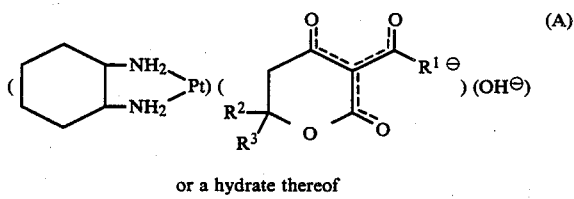

or a hydrate thereof wherein $R^1$ is an alkyl group having 1 to 18 carbon atoms, an alkenyl group having up to 18 carbon atoms or a group —X—$R^5$ in which X represents —CH=CH— or an alkylene group having 1 to 5 carbon atoms, and $R^5$ is a phenyl group, a hydroxyphenyl group, an alkoxyphenyl group having 7 to 12 carbon atoms, a halogenophenyl group, a nitrophenyl group, an alkoxycarbonylphenyl group having 8 to 13 carbon atoms, a cyclohexyl group having an alkyl substituent having 1 to 5 carbon atoms, or a group represented by the formula:

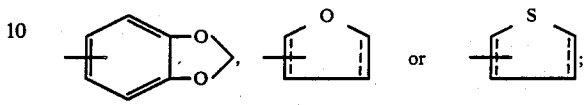

$R^2$ is an alkyl group having 1 to 18 carbon atoms, $R^3$ is a hydrogen atom, or $R^2$ and $R^3$ are linked together to form an alkylene group having 2 to 7 carbon atoms; the dotted line indicates that the bond may be either a single bond or a double bond; the chain line indicates a conjugated system; and the 1,2-diaminocyclohexane moiety has a cis-, trans-l- or trans-d-configuration.

2. A platinum complex of claim 1, which is 3-acetyl-6-methylterahydropyran-2,4-dione-hydroxo(trans-l-1,2-diaminocyclohexane)platinum (II) monohydrate having the formula:

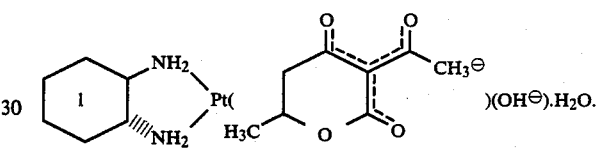

3. A platinum complex of claim 1, which is 3-acetyl-6-methyl-2H-pyran-2,4(3H)-dione-hydroxo(trans-l-1,2-diaminocyclohexane)platinum (II) monohydrate having the formula:

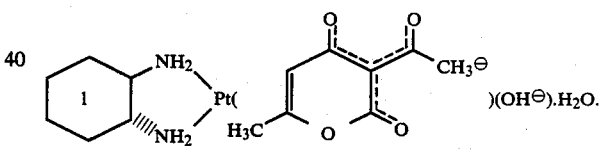

4. A platinum complex of claim 1, which is 3-[3-(2-tetrahydrofuryl)propionyl]-6-methyltetrahydropyran-2,4-dione-hydroxo(trans-l-1,2-diaminocyclohexane)-platinum (II) monohydrate having the formula:

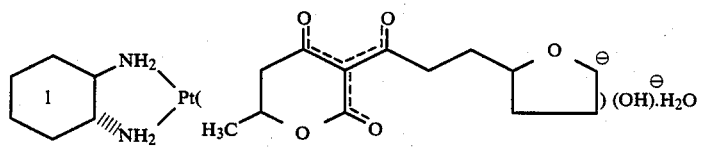

5. A platinum complex of claim 1, which is 3-(2-thienylacryloyl)-6-methyl-2H-pyran-2,4(3H)-dione-hydroxo(trans-l-1,2-diaminocyclohexane)platinum (II) hemihydrate having the formula:

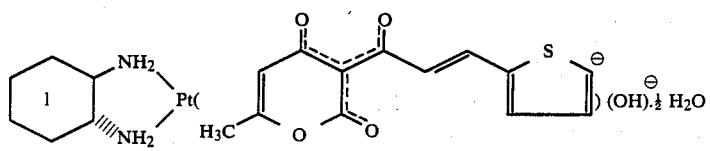

6. A platinum complex of claim 1, which is 3-decanoyl-6-methyltetrahydropyran-2,4-dione-hydroxo(trans-l-1,2-diaminocyclohexane)platinum (II) having the formula:

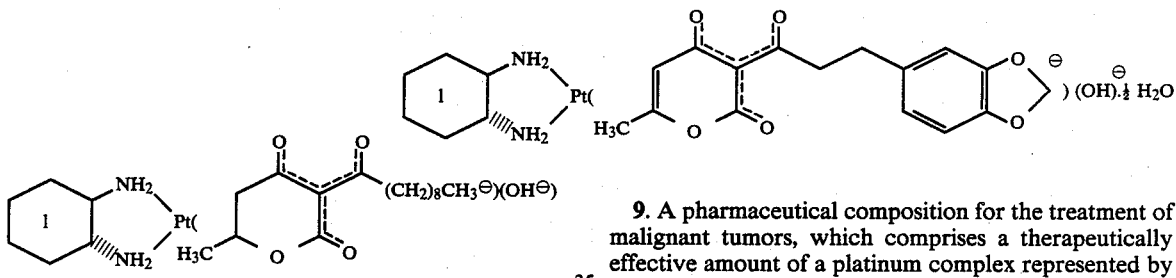

7. A platinum complex of claim 1, which is 3-[3-(m-hydroxyphenyl)propionyl]-6-methyl-2H-pyran-2,4(3H)-dione-hydroxo(trans-l-1,2-diaminocyclohexane)platinum (II) having the formula:

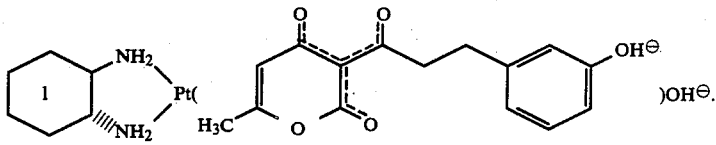

8. A platinum complex of claim 1, which is 3-[3-(3,4-methylene-dioxyphenyl)propionyl]-6-methyl-2H-pyran-2,4(3H)-dione-hydroxo(trans-l-1,2-diaminocyclohexane)platinum (II) hemihydrate having the formula:

9. A pharmaceutical composition for the treatment of malignant tumors, which comprises a therapeutically effective amount of a platinum complex represented by the general formula (A) of claim 1 and a pharmaceutically acceptable carrier therefor.

* * * * *

UNITED STATES PATENT AND TRADEMARK OFFICE
CERTIFICATE OF CORRECTION

PATENT NO. : 4,912,100

DATED : March 27, 1990

INVENTOR(S) : Masaji Ohno, Masato Mutoh, Hisao Kondo, Keiichi Matsunaga

It is certified that error appears in the above-identified patent and that said Letters Patent is hereby corrected as shown below:

Column 3, Between lines 35 and 40, change " 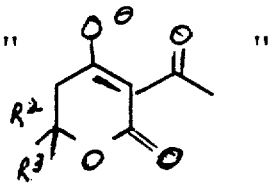 "

to -- 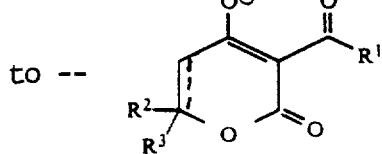

Column 6, line 55, after "2,4-dione)" insert -- - --.

Column 7, line 67, after "2,4-dione) insert -- - --.

Column 8, line 1, after "2,4(3H)-dione" insert -- - --.

Signed and Sealed this

Seventh Day of April, 1992

Attest:

HARRY F. MANBECK, JR.

*Attesting Officer*  *Commissioner of Patents and Trademarks*